United States Patent
Bhattacharyya et al.

(10) Patent No.: US 11,441,196 B2
(45) Date of Patent: Sep. 13, 2022

(54) RIBOSOMAL RIBONUCLEIC ACID HYBRIDIZATION FOR ORGANISM IDENTIFICATION

(71) Applicants: THE BROAD INSTITUTE, INC., Cambridge, MA (US); THE GENERAL HOSPITAL CORPORATION, Boston, MA (US)

(72) Inventors: Roby Bhattacharyya, Cambridge, MA (US); Deborah Hung, Lexington, MA (US); Jonathan Livny, Cambridge, MA (US)

(73) Assignees: THE BROAD INSTITUTE, INC., Cambridge, MA (US); THE GENERAL HOSPITAL CORPORATION, Boston, MA (US)

( * ) Notice: Subject to any disclaimer, the term of this patent is extended or adjusted under 35 U.S.C. 154(b) by 231 days.

(21) Appl. No.: 14/775,296

(22) PCT Filed: Mar. 14, 2014

(86) PCT No.: PCT/US2014/027158
§ 371 (c)(1),
(2) Date: Sep. 11, 2015

(87) PCT Pub. No.: WO2014/152281
PCT Pub. Date: Sep. 25, 2014

(65) Prior Publication Data
US 2016/0032364 A1 Feb. 4, 2016

Related U.S. Application Data

(60) Provisional application No. 61/794,544, filed on Mar. 15, 2013.

(51) Int. Cl.
*C12Q 1/689* (2018.01)

(52) U.S. Cl.
CPC ........ *C12Q 1/689* (2013.01); *C12Q 2600/112* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 6,399,364 B1 | 6/2002 | Reeve | |
| 7,087,742 B1* | 8/2006 | Hogan | C12Q 1/689 536/24.3 |
| 2004/0029129 A1 | 2/2004 | Wang et al. | |
| 2006/0046246 A1 | 3/2006 | Zeng et al. | |
| 2009/0035329 A1 | 2/2009 | Blaser et al. | |
| 2012/0264637 A1* | 10/2012 | Wiener-Kronish | C12Q 1/6883 506/9 |

FOREIGN PATENT DOCUMENTS

WO   WO 2010/151842   * 12/2010   ............ C12Q 1/68

OTHER PUBLICATIONS

Smith et al., Mol Biol, Evol, 16(6)773-782, 1999, pp. 773-783.*
Rogers et al., PNAS, 1983, vol. 82, pp. 1160-1164.*
International Preliminary Report on Patentability for PCT/US2014/027158, dated Sep. 24, 2015, 9 pages.
Bausch, "Office Action issued in U.S. Appl. No. 15/294,015, filed Oct. 14, 2016", dated Mar. 29, 2018, 1-10.
Ahern, Holly, "Biochemical, Reagent Kits Offer Scientists Good Return on Investment", The Scientist, pp. 21-22, Jul. 24, 1995.
International Search Report and Written Opinion dated Oct. 1, 2014 for PCT/US2014/027158, dated Oct. 1, 2014, 1-18.

* cited by examiner

*Primary Examiner* — Sarae L Bausch
(74) *Attorney, Agent, or Firm* — F. Brent Nix, Esq.; Johnson, Marcou, Isaacs & Nix, LLC

(57) ABSTRACT

The present disclosure relates to method of distinguishing between two or more species of one or more organisms in a sample, by contacting a biological sample comprising ribosomal ribonucleic acid (rRNA) with a set of antisense probes, wherein the set of probes contains at least one detectable probe that is specific for a target rRNA sequence of each species to be tested, and wherein the individual probes specific for each species comprises less than about 85% sequence identity; and, detecting hybridization between one or more of the probes and the rRNA, thereby distinguishing between two or more species in a sample.

10 Claims, 3 Drawing Sheets

Specification includes a Sequence Listing.

FIG. 3

SPECIES-SPECIFIC_PROBE

| Probe | E_coli | (col2) | E_faecalis | E_faecium | P_aeruginosa | S_aureus | (col7) | (col8) | (col9) |
|---|---|---|---|---|---|---|---|---|---|
| 1... | 4913.43 | 51.64 | 253.18 | 19.86 | 8.97 | -6.15 | 18.20 | 171.64 | 150.62 |
| 2... | 13559.79 | 48.89 | 245.31 | 21.67 | 3.12 | 7.96 | 70.53 | 243.80 | 184.84 |
| 14 E_col_16S_2 | 84.60 | 4512.26 | 108.97 | 28.93 | 17.33 | -12.19 | 14.04 | 93.21 | 29.52 |
| 17 E_col_23S | 220.02 | 3526.31 | 223.03 | 135.95 | 120.96 | 84.50 | 106.26 | 168.51 | 153.25 |
| 5... | 1.05 | -4.26 | 4397.06 | -5.54 | 258.03 | -52.48 | -14.20 | 107.85 | 4.95 |
| 8... | 1.05 | -8.84 | -6.39 | 20182.93 | -10.25 | -67.59 | -18.36 | -8.23 | 19.87 |
| 9 E_fcm_16S | 1.05 | -9.75 | -7.70 | -10.07 | -10.25 | -70.61 | -20.02 | -6.14 | -13.47 |
| 10 E_fcm_23S | 3.93 | -6.09 | -5.08 | 2109.54 | -4.40 | -61.54 | -10.05 | -5.09 | -7.33 |
| 23 | 12.58 | -5.17 | 261.04 | 8.07 | 1379.66 | -64.56 | -5.90 | 469.69 | -1.19 |
| 26 P_aer_23S.1 | 738.63 | 548.28 | 1590.34 | 196.72 | 72.49 | 9673.38 | 270.75 | 1376.36 | 991.24 |
| 28 P_aer_16S.1 | 217.14 | 123.11 | 347.57 | 42.53 | 13.15 | 1323.97 | 73.86 | 365.11 | 246.26 |
| 29 P_aer_16S.2 | 1911.26 | 488.72 | 1488.08 | 164.98 | 96.73 | 9270.24 | 310.62 | 1344.99 | 1026.33 |
| 30 P_aer_23S.2 | 652.19 | 343.94 | 924.38 | 118.72 | 65.80 | 6349.74 | 254.96 | 1036.49 | 695.53 |
| 32 P_aer_23S.4 | 640.67 | 464.90 | 1333.39 | 208.51 | 89.20 | 10023.66 | 261.61 | 2321.73 | 842.94 |
| 27 | 6.81 | -9.75 | -7.70 | -6.44 | -10.25 | 24543.64 | -15.03 | -7.18 | -16.98 |
| 42 S_aur_16S | 6.81 | 0.33 | 73.58 | 1.72 | -5.24 | -55.50 | 9494.66 | 43.01 | 11.97 |
| 39 S_aur_23S | 18.34 | 6.74 | 93.24 | 5.35 | -5.48 | -56.51 | 9107.52 | 67.07 | 33.03 |
| 53 S_aur_5S | 142.23 | 52.56 | 410.49 | 78.81 | 11.54 | 303.07 | 33097.33 | 424.72 | 220.81 |
| 40 | 15.46 | -6.09 | 4.10 | -1.91 | 130.16 | -65.57 | -17.53 | 809.56 | -16.11 |
| 41 | 26.98 | -7.92 | 11.97 | -6.44 | -8.58 | -63.56 | -14.20 | 8599.44 | -10.84 |
| 37 | 21.22 | 4.91 | 2.79 | 13.51 | -10.25 | -53.48 | -9.22 | 9.55 | 39612.38 |
| 38 | 81.72 | 14.99 | 84.07 | 3.53 | -3.57 | -47.44 | -10.88 | 54.52 | 23076.38 |

RIBOSOMAL RIBONUCLEIC ACID HYBRIDIZATION FOR ORGANISM IDENTIFICATION

CROSS-REFERENCE TO RELATED APPLICATION

This application is the U.S. National Stage of International Application No. PCT/US2014/027158, filed Mar. 14, 2014, published in English under PCT Article 21(2), which claims the priority benefit of the earlier filing date of U.S. Provisional Application No. 61/794,544, filed Mar. 15, 2013, which is hereby specifically incorporated herein by reference in its entirety.

FEDERALLY SPONSORED RESEARCH OR DEVELOPMENT

This invention was made with Government support under Grant number HHSN272200900018C awarded by the National Institutes of Health. The Government has certain rights in the invention.

FIELD OF THE INVENTION

The present disclosure relates generally to a hybridization-based method of rapidly detecting and identifying infectious disease pathogens, the probes for detecting one or more types of pathogens, as well as kits including the probes.

BACKGROUND OF THE INVENTION

Identification of bacterial pathogens that cause infection is a key first step in devising an informed, effective treatment strategy. To effectively treat bacterial pathogen infection, it is necessary to begin treatment as early as possible in the in the development of the infection, ideally upon onset of clinical symptoms. Current microbiologic methods rely on growth of these pathogens in culture, followed by subculture and biochemical assays to determine pathogen identity, a process that typically takes over 48 hours from the time cultures are drawn. Partial information is often available earlier, at the time a culture is recognized to be positive, by Gram's stain; for blood cultures this still requires 12 hours to several days. While Gram's stain characteristics can guide treatment to some extent, much more information about the expected course of infection and possible treatments is available from full organism identification. More rapid organism identification would permit clinicians to make informed decisions earlier in a patient's course, which in turn is known to greatly reduce mortality in serious infections.

The reliance on slow culture methods is particularly problematic in view of the current crisis of antibiotic resistance of many pathogens. A molecular tool capable of rapidly diagnosing the pathogen and its drug resistance profile will transform the management of bacterial, fungal, viral, and parasitic infections and will decrease mortality, control health care costs, and improve overall public health.

Current efforts at molecular diagnostics have centered on DNA recognition through PCR amplification, or recognition of protein signatures through mass spectrometry. PCR-based techniques have the advantage of amplification of signal, potentially permitting earlier detection. However, polymerases used in PCR are relatively intolerant to the biochemical milieu of many clinical samples, requiring processing steps that introduce delays and the possibility of false negative results. Further, the extrinsic amplification step introduces the possibility of false positives as well. Mass spectrometry is limited in recognition by the need to unambiguously recognize peptide signatures that have less inherent distinction from human or environmental material that may be present in a sample.

Clinically, bloodstream infections come to clinical attention at a time when the bacterial burden is very low, with best estimates in the range of 10 to 100 organisms per mL of blood for many common pathogens. The relative abundance of rRNA (estimated at thousands of fold more abundant than even the most abundant mRNAs) makes it an excellent candidate for early detection of organisms. This intrinsic amplification step minimizes the need for extrinsic amplification in the detection assay, making it conceptually more streamlined and less error-prone.

Ribosomal RNA (rRNA) sequences (in bacteria, 16S, 23S, and 5S subunits) may be used for phylogenetic assignment of organisms, particularly the 16S subunit. The bacterial 16S and 23S rRNA subunits have stretches of highly conserved regions that can identify an organism as a member of the bacterial kingdom and other higher-order phylogeny assignments, and more variable regions that can be used to identify organisms at the level of genus and species, which inform clinical decision-making Because of their central role in the fundamental biological process of protein translation, even these regions that vary between bacterial species remain tightly conserved within a species. Furthermore, these rRNA subunits are vastly more abundant than any other RNA species within a cell; taken together, ribosomal RNA makes up >90% of the RNA mass in a bacterial cell.

One challenge to rRNA-based diagnosis (as opposed to rDNA, or mRNA) has been that these rRNA molecules have tight secondary structural elements that limit their ability to be recognized by hybridization. The high degree of sequence conservation poses a second challenge in using rRNA recognition to discriminate between species: the method of choice must recognize all members of a given species to be fully sensitive in a clinical setting, but must not cross-react against other species for optimal specificity. However, if these challenges can be overcome, rRNA recognition has the potential to permit detection of even a very small number of bacteria because of the massive amplification of this gene that naturally occurs in vivo: best estimates suggest that 16S and 23S rRNA are present at $10^4$ copies per cell, more than 100-fold more abundant than even the highest-expressed mRNAs.

In large part because of these challenges, most current efforts at bacterial speciation based on rRNA have focused on sequencing of the DNA gene that encodes this structural RNA. This approach typically requires PCR amplification of the gene in question and therefore suffers the same limitations as other PCR-based clinical diagnostics, discussed above. Furthermore, focusing on the DNA copies of these rRNA genes removes one of the major advantages of working with rRNA; namely, its intrinsic abundance.

Accordingly, a need exists for a rapid method of detecting and identifying infectious disease pathogens. A point of care test that provides sensitive, specific detection of bacterial pathogen types and subtypes in a relatively short time is needed, so that diagnosis is completed in sufficient time to permit effective treatment of an infected person.

SUMMARY

The present disclosure relates to methods of detecting the presence of a pathogen in a sample, such as a biological sample obtained from a subject. Disclosed is a hybridization-based method to identify bacterial species based on annealing to the ribosomal RNA present in lysates. These lysates may in principle be derived from axenic culture, clinical specimens, environmental or industrial samples, or elsewhere. In some embodiments, the technique employs a commercial RNA recognition technology known as Nanostring, which heretofore has largely been applied to characterization of messenger RNA (mRNA) transcripts.

The sequences of annotated 16S rRNA-encoding genes were extracted from the NCBI database of fully sequenced bacterial genomes. 16S rRNA sequences derived from all strains of interest were examined to identify regions that were conserved among strains of the same species but significantly divergent among different species to allow for selective hybridization. These regions were then targeted for hybridization-based detection using NanoString's method of two DNA oligonucleotides that bind to adjacent 50-nucleotide stretches of RNA. When the target transcript is present in a lysate, it links a biotinylated DNA oligo (the "capture probe") to an adjacent fluorescently labeled DNA oligo (the "reporter probe").

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

FIG. 3 is a heatmap.

BRIEF DESCRIPTION OF THE SEQUENCES

Figure 1:
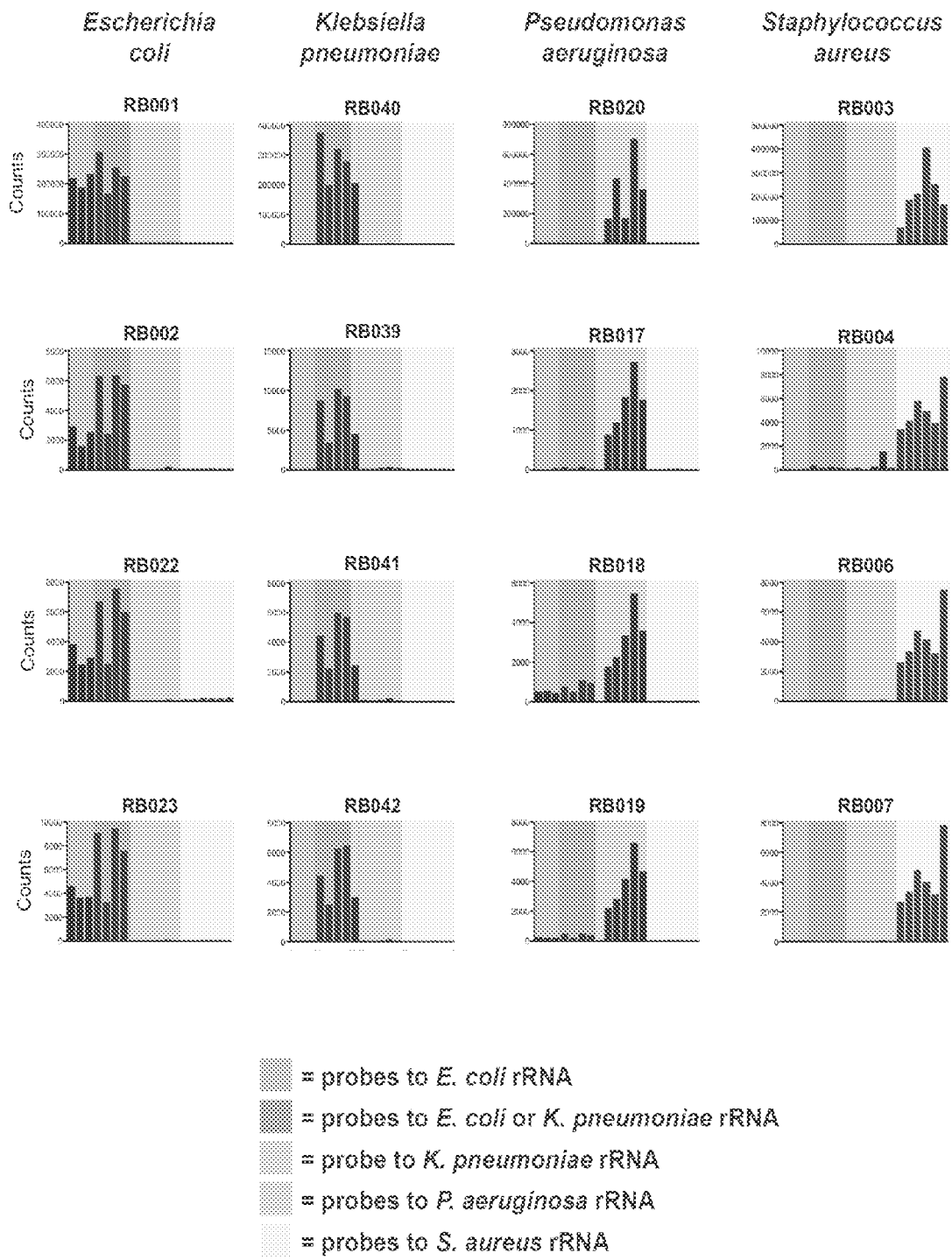
FIG. 1 are graphs of the results of the probe sets of 16 clinical isolates of four major clinical pathogens: *Escherichia coli, Klebsiella pneumoniae, Pseudomonas aeruginosa*, or *Staphylococcus aureus*.

The nucleic acid sequences shown herein are shown using standard letter abbreviations for nucleotide bases, as defined in 37 C.F.R. 1.822. Only one strand of each nucleic acid sequence is shown, but the complementary strand is understood as included by any reference to the displayed strand. The Sequence Listing is submitted as an ASCII text file in the form of the file named BROD_0230_ST25.txt, which was created on Mar. 13, 2014, and is 29 kilobytes, which is incorporated by reference herein.

DETAILED DESCRIPTION OF SEVERAL EMBODIMENTS

II. Summary of Terms

Unless otherwise noted, technical terms are used according to conventional usage. Definitions of common terms in molecular biology can be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710); and other similar references.

As used herein, the singular forms "a," "an," and "the," refer to both the singular as well as plural, unless the context clearly indicates otherwise. For example, the term "a probe" includes single or plural probes and can be considered equivalent to the phrase "at least one probe."

As used herein, the term "comprises" means "includes." Thus, "comprising a probe" means "including a probe" without excluding other elements.

It is further to be understood that all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments of the invention, the following explanations of terms are provided:

Animal: A living multi-cellular vertebrate or invertebrate organism, a category that includes, for example, mammals. The term mammal includes both human and non-human mammals. Similarly, the term "subject" includes both human and veterinary subjects.

Amplification: To increase the number of copies of a nucleic acid molecule. The resulting amplification products are called "amplicons." Amplification of a nucleic acid molecule (such as a DNA or RNA molecule) refers to use of a technique that increases the number of copies of a nucleic acid molecule in a sample. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. The product of amplification can be characterized by such techniques as electrophoresis, restriction endonuclease cleavage patterns, oligonucleotide hybridization or ligation, and/or nucleic acid sequencing.

Other examples of in vitro amplification techniques include quantitative real-time PCR, reverse transcriptase PCR, real-time reverse transcriptase PCR (rt RT-PCR), nested PCR, strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Bacterial pathogen: A bacteria that causes disease (pathogenic bacteria). Examples of pathogenic bacteria that can be detected in accordance with the disclosed methods include without limitation any one or more of (or any combination of) *Acinetobacter baumanii, Actinobacillus* sp., *Actinomycetes, Actinomyces* sp. (such as *Actinomyces israelii* and *Actinomyces naeslundii*), *Aeromonas* sp. (such as *Aeromonas hydrophile, Aeromonas veronii* biovar sobria (*Aeromonas sobria*), and *Aeromonas caviae*), *Anaplasma phagocytophilum, Anaplasma marginal*, e *Alcaligenes xylosoxidans, Acinetobacter baumanii, Actinobacillus actinomycetemcomitans, Bacillus* sp. (such as *Bacillus anthracis, Bacillus*

*cereus, Bacillus subtilis, Bacillus thuringiensis,* and *Bacillus stearothermophilus*), *Bacteroides* sp. (such as *Bacteroides fragilis*), *Bartonella* sp. (such as *Bartonella bacilliformis* and *Bartonella henselae, Bifidobacterium* sp., *Bordetella* sp. (such as *Bordetella pertussis, Bordetella parapertussis,* and *Bordetella bronchiseptica*), *Borrelia* sp. (such as *Borrelia recurrentis,* and *Borrelia burgdorferi*), *Brucella* sp. (such as *Brucella abortus, Brucella canis, Brucella melintensis* and *Brucella suis*), *Burkholderia* sp. (such as *Burkholderia pseudomallei* and *Burkholderia cepacia*), *Campylobacter* sp. (such as *Campylobacter jejuni, Campylobacter coli, Campylobacter lari* and *Campylobacter fetus*), *Capnocytophaga* sp., *Cardiobacterium hominis, Chlamydia trachomatis, Chlamydophila pneumoniae, Chlamydophila psittaci, Citrobacter* sp. *Coxiella burnetii, Corynebacterium* sp. (such as, *Corynebacterium diphtheriae, Corynebacterium jeikeum* and *Corynebacterium*), *Clostridium* sp. (such as *Clostridium perfringens, Clostridium difficile, Clostridium botulinum* and *Clostridium tetani*), *Eikenella corrodens, Enterobacter* sp. (such as *Enterobacter aerogenes, Enterobacter agglomerans, Enterobacter cloacae* and *Escherichia coli*, including opportunistic *Escherichia coli*, such as enterotoxigenic *E. coli*, enteroinvasive *E. coli*, enteropathogenic *E. coli*, enterohemorrhagic *E. coli*, enteroaggregative *E. coli* and uropathogenic *E. coli*) *Enterococcus* sp. (such as *Enterococcus faecalis* and *Enterococcus faecium*) *Ehrlichia* sp. (such as *Ehrlichia chafeensia* and *Ehrlichia canis*), *Erysipelothrix rhusiopathiae, Eubacterium* sp., *Francisella tularensis, Fusobacterium nucleatum, Gardnerella vaginalis, Gemella morbillorum, Haemophilus* sp. (such as *Haemophilus influenzae, Haemophilus ducreyi, Haemophilus aegyptius, Haemophilus parainfluenzae, Haemophilus haemolyticus* and *Haemophilus parahaemolyticus, Helicobacter* sp. (such as *Helicobacter pylori, Helicobacter cinaedi* and *Helicobacter fennelliae*), *Kingella kingii, Klebsiella* sp. (such as *Klebsiella pneumoniae, Klebsiella granulomatis* and *Klebsiella oxytoca*), *Lactobacillus* sp., *Listeria monocytogenes, Leptospira interrogans, Legionella pneumophila, Leptospira interrogans, Peptostreptococcus* sp., *Mannheimia hemolytica, Moraxella catarrhalis, Morganella* sp., *Mobiluncus* sp., *Micrococcus* sp., *Mycobacterium* sp. (such as *Mycobacterium leprae, Mycobacterium tuberculosis, Mycobacterium paratuberculosis, Mycobacterium intracellulare, Mycobacterium avium, Mycobacterium bovis,* and *Mycobacterium marinum*), *Mycoplasm* sp. (such as *Mycoplasma pneumoniae, Mycoplasma hominis,* and *Mycoplasma genitalium*), *Nocardia* sp. (such as *Nocardia asteroides, Nocardia cyriacigeorgica* and *Nocardia brasiliensis*), *Neisseria* sp. (such as *Neisseria gonorrhoeae* and *Neisseria meningitidis*), *Pasteurella multocida, Plesiomonas shigelloides. Prevotella* sp., *Porphyromonas* sp., *Prevotella melaninogenica, Proteus* sp. (such as *Proteus vulgaris* and *Proteus mirabilis*), *Providencia* sp. (such as *Providencia alcalifaciens, Providencia rettgeri* and *Providencia stuartii*), *Pseudomonas aeruginosa, Propionibacterium acnes, Rhodococcus equi, Rickettsia* sp. (such as *Rickettsia rickettsii, Rickettsia akari* and *Rickettsia prowazekii, Orientia tsutsugamushi* (formerly: *Rickettsia tsutsugamushi*) and *Rickettsia typhi*), *Rhodococcus* sp., *Serratia marcescens, Stenotrophomonas maltophilia, Salmonella* sp. (such as *Salmonella enterica, Salmonella typhi, Salmonella paratyphi, Salmonella enteritidis, Salmonella cholerasuis* and *Salmonella typhimurium*), *Serratia* sp. (such as *Serratia marcesans* and *Serratia liquifaciens*), *Shigella* sp. (such as *Shigella dysenteriae, Shigella flexneri, Shigella boydii* and *Shigella sonnei*), *Staphylococcus* sp. (such as *Staphylococcus aureus, Staphylococcus epidermidis, Staphylococcus hemolyticus, Staphylococcus saprophyticus*), *Streptococcus* sp. (such as *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae, Streptococcus mutans, Streptococcus pyogenes,* Group A streptococci, *Streptococcus pyogenes,* Group B streptococci, *Streptococcus agalactiae,* Group C streptococci, *Streptococcus anginosus, Streptococcus equismilis,* Group D streptococci, *Streptococcus bovis,* Group F streptococci, and *Streptococcus anginosus* Group G streptococci), *Spirillum minus, Streptobacillus moniliformi, Treponema* sp. (such as *Treponema carateum, Treponema petenue, Treponema pallidum* and *Treponema endemicum, Tropheryma whippelii, Ureaplasma urealyticum, Veillonella* sp., *Vibrio* sp. (such as *Vibrio cholerae, Vibrio parahemolyticus, Vibrio vulnificus, Vibrio parahaemolyticus, Vibrio vulnificus, Vibrio alginolyticus, Vibrio mimicus, Vibrio hollisae, Vibrio fluvialis, Vibrio metchnikovii, Vibrio damsela* and *Vibrio furnisii*), *Yersinia* sp. (such as *Yersinia enterocolitica, Yersinia pestis,* and *Yersinia pseudotuberculosis*) and *Xanthomonas maltophilia* among others.

cDNA (complementary DNA): A piece of DNA lacking internal, non-coding segments (introns) and transcriptional regulatory sequences. cDNA also can contain untranslated regions (UTRs) that are responsible for translational control in the corresponding RNA molecule. cDNA can be synthesized in the laboratory by reverse transcription from RNA.

Change: To become different in some way, for example to be altered, such as increased or decreased. A detectable change is one that can be detected, such as a change in the intensity, frequency or presence of an electromagnetic signal, such as fluorescence. In some examples, the detectable change is a reduction in fluorescence intensity. In some examples, the detectable change is an increase in fluorescence intensity.

Complementary: A double-stranded DNA or RNA strand consists of two complementary strands of base pairs. Complementary binding occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA. In this example, the sequence 5'-ATCG-3' is the reverse complement of 3'-TAGC-5'. Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions.

Detect: To determine if an agent (such as a signal or particular nucleotide or amino acid) is present or absent. In some examples, this can further include quantification. For example, use of the disclosed probes in particular examples permits detection of a fluorophore, for example detection of a signal from an acceptor fluorophore.

Electromagnetic radiation: A series of electromagnetic waves that are propagated by simultaneous periodic variations of electric and magnetic field intensity, and that includes radio waves, infrared, visible light, ultraviolet light, X-rays and gamma rays. In particular examples, electromagnetic radiation is emitted by a laser, which can possess properties of monochromaticity, directionality, coherence, polarization, and intensity. Lasers are capable of emitting light at a particular wavelength (or across a relatively narrow range of wavelengths), for example such that energy from the laser can excite a donor but not an acceptor fluorophore.

Emission or emission signal: The light of a particular wavelength generated from a fluorophore after the fluorophore absorbs light at its excitation wavelengths.

Excitation or excitation signal: The light of a particular wavelength necessary to excite a fluorophore to a state such that the fluorophore will emit a different (such as a longer) wavelength of light.

Fluorophore: A chemical compound, which when excited by exposure to a particular stimulus such as a defined wavelength of light, emits light (fluoresces), for example at a different wavelength (such as a longer wavelength of light). Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) eliminates the need for an external source of electromagnetic radiation, such as a laser. Examples of particular fluorophores that can be used in the probes disclosed herein are provided in U.S. Pat. No. 5,866,366 to Nazarenko et al., such as 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcoumuarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron® Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives; LightCycler Red 640; Cy5.5; and Cy56-carboxyfluorescein; 5-carboxyfluorescein (5-FAM); boron dipyrromethene difluoride (BODIPY); N,N,N',N'-tetramethyl-6-carboxyrhodamine (TAMRA); acridine, stilbene, -6-carboxy-fluorescein (HEX), TET (Tetramethyl fluorescein), 6-carboxy-X-rhodamine (ROX), Texas Red, 2',7'-dimethoxy-4',5'-dichloro-6-carboxyfluorescein (JOE), Cy3, Cy5, VIC® (Applied Biosystems), LC Red 640, LC Red 705, Yakima yellow amongst others.

Other suitable fluorophores include those known to those skilled in the art, for example those available from Molecular Probes (Eugene, Oreg.). In particular examples, a fluorophore is used as a donor fluorophore or as an acceptor fluorophore. "Acceptor fluorophores" are fluorophores which absorb energy from a donor fluorophore, for example in the range of about 400 to 900 nm (such as in the range of about 500 to 800 nm). Acceptor fluorophores generally absorb light at a wavelength which is usually at least 10 nm higher (such as at least 20 nm higher), than the maximum absorbance wavelength of the donor fluorophore, and have a fluorescence emission maximum at a wavelength ranging from about 400 to 900 nm. Acceptor fluorophores have an excitation spectrum which overlaps with the emission of the donor fluorophore, such that energy emitted by the donor can excite the acceptor. Ideally, an acceptor fluorophore is capable of being attached to a nucleic acid molecule.

In a particular example, an acceptor fluorophore is a dark quencher, such as, Dabcyl, QSY7 (Molecular Probes), QSY33 (Molecular Probes), BLACK HOLE QUENCHERS™ (Glen Research), ECLIPSE™ Dark Quencher (Epoch Biosciences), IOWA BLACK™ (Integrated DNA Technologies). A quencher can reduce or quench the emission of a donor fluorophore. In such an example, instead of detecting an increase in emission signal from the acceptor fluorophore when in sufficient proximity to the donor fluorophore (or detecting a decrease in emission signal from the acceptor fluorophore when a significant distance from the donor fluorophore), an increase in the emission signal from the donor fluorophore can be detected when the quencher is a significant distance from the donor fluorophore (or a decrease in emission signal from the donor fluorophore when in sufficient proximity to the quencher acceptor fluorophore). "Donor Fluorophores" are fluorophores or luminescent molecules capable of transferring energy to an acceptor fluorophore, thereby generating a detectable fluorescent signal from the acceptor. Donor fluorophores are generally compounds that absorb in the range of about 300 to 900 nm, for example about 350 to 800 nm. Donor fluorophores have a strong molar absorbance coefficient at the desired excitation wavelength, for example greater than about $10^3$ $M^{-1}$ $cm^{-1}$.

Fluorescence Resonance Energy Transfer (FRET): A spectroscopic process by which energy is passed between an initially excited donor to an acceptor molecule separated by 10-100 Å. The donor molecules typically emit at shorter wavelengths that overlap with the absorption of the acceptor molecule. The efficiency of energy transfer is proportional to the inverse sixth power of the distance (R) between the donor and acceptor ($1/R^6$) fluorophores and occurs without emission of a photon. In applications using FRET, the donor and acceptor dyes are different, in which case FRET can be detected either by the appearance of sensitized fluorescence of the acceptor or by quenching of donor fluorescence. For example, if the donor's fluorescence is quenched it indicates the donor and acceptor molecules are within the Förster radius (the distance where FRET has 50% efficiency, about 20-60 Å), whereas if the donor fluoresces at its characteristic wavelength, it denotes that the distance between the donor and acceptor molecules has increased beyond the Förster radius, such as when a TAQMAN® probe is degraded by Taq polymerase following hybridization of the probe to a target nucleic acid sequence or when a hairpin probe is hybridized to a target nucleic acid sequence. In another example, energy is transferred via FRET between two different fluorophores such that the acceptor molecule can emit light at its characteristic wavelength, which is always longer than the emission wavelength of the donor molecule. Examples of oligonucleotides using FRET that can be used to detect amplicons include linear oligoprobes, such as HybProbes, 5' nuclease oligoprobes, such as TAQMAN® probes, hairpin oligoprobes, such as molecular beacons, scorpion primers and UniPrimers, minor groove binding probes, and self-fluorescing amplicons, such as sunrise primers.

Fungal pathogen: A fungus that causes disease. Examples of fungal pathogens detectable with the disclosed methods include without limitation *Trichophyton rubrum, T. mentagrophytes, Epidermophyton floccosum, Microsporum canis, Pityrosporum orbiculare (Malassezia furfur), Candida* sp. (such as *Candida albicans*), *Aspergillus* sp. (such as *Aspergillus fumigatus, Aspergillus flavus* and *Aspergillus clavatus*), *Cryptococcus* sp. (such as *Cryptococcus neoformans, Cryptococcus gattii, Cryptococcus laurentii* and *Cryptococcus albidus*), *Histoplasma* sp. (such as *Histoplasma capsulatum*), *Pneumocystis* sp. (such as *Pneumocystis jirovecii*), and *Stachybotrys* (such as *Stachybotrys chartarum*) among others.

Hybridization: Oligonucleotides and their analogs hybridize by hydrogen bonding, which includes Watson-Crick, Hoogsteen or reversed Hoogsteen hydrogen bonding, between complementary bases. Generally, nucleic acid consists of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

The ability of complementary single-stranded DNA or RNA to form a duplex molecule (also referred to as a hybridization complex). Nucleic acid hybridization techniques can be used to form hybridization complexes between a probe or primer and a nucleic acid, such as a ribonucleic acid. Hybridization occurs between a single stranded probe and a single stranded target ribonucleic acid. "Specifically hybridizable" and "specifically complementary" are terms that indicate a sufficient degree of complementarity such that stable and specific binding occurs between the oligonucleotide (or its analog) and the DNA or RNA target. The oligonucleotide or oligonucleotide analog need not be 100% complementary to its target sequence to be specifically hybridizable. An oligonucleotide or analog is specifically hybridizable when there is a sufficient degree of complementarity to avoid non-specific binding of the oligonucleotide or analog to non-target sequences under conditions where specific binding is desired. Such binding is referred to as specific hybridization.

Hybridization conditions resulting in particular degrees of stringency will vary depending upon the nature of the hybridization method and the composition and length of the hybridizing nucleic acid sequences. Generally, the temperature of hybridization and the ionic strength (such as the Na+ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (detects sequences that share at least 90% identity)
Hybridization: 5×SSC at 65° C. for 16 hours
Wash twice: 2×SSC at room temperature (RT) for 15 minutes each
Wash twice: 0.5×SSC at 65° C. for 20 minutes each
High Stringency (detects sequences that share at least 80% identity)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each
Low Stringency (detects sequences that share at least 50% identity)
Hybridization: 6×SSC at RT to 55° C. for 16-20 hours
Wash at least twice: 2×-3×SSC at RT to 55° C. for 20-30 minutes each.

The probes and primers disclosed herein can hybridize under low stringency, high stringency, and very high stringency conditions.

Isolated: An "isolated" biological component (such as a protein, a nucleic acid probe, such as the probes and target nucleic acids described herein) has been substantially separated or purified away from other biological components in the cell of the organism in which the component naturally occurs, for example, extra-chromatin DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids. It is understood that the term "isolated" does not imply that the biological component is free of trace contamination, and can include nucleic acid molecules that are at least 50% isolated, such as at least 75%, 80%, 90%, 95%, 98%, 99%, or even 100% isolated.

Label: An agent capable of detection, for example by spectrophotometry, flow cytometry, or microscopy. For example, a label can be attached to a nucleotide, thereby permitting detection of the nucleotide, such as detection of the nucleic acid molecule of which the nucleotide is a part. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N. Y., 1989) and Ausubel et al. (In Current Protocols in Molecular Biology, John Wiley & Sons, New York, 1998).

Nucleic acid (molecule or sequence): A deoxyribonucleotide or ribonucleotide polymer including, without limitation, cDNA, mRNA, genomic DNA, and synthetic (such as chemically synthesized) DNA or RNA or hybrids thereof. The nucleic acid can be double-stranded (ds) or single-stranded (ss). Where single-stranded, the nucleic acid can be the sense strand or the antisense strand. Nucleic acids can include natural nucleotides (such as A, T/U, C, and G), and can also include analogs of natural nucleotides, such as labeled nucleotides. Some examples of nucleic acids include the probes disclosed herein.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U). Nucleotides include those nucleotides containing modified bases, modified sugar moieties, and modified phosphate backbones, for example, as described in U.S. Pat. No. 5,866,336 to Nazarenko et al.

Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N-6-sopentenyladenine, 1-methylguanine, 1-methylinosine, 2,2-dimethylguanine, 2-methyladenine, 2-methylguanine, 3-methylcytosine, 5-methyl cytosine, N6-adenine, 7-methylguanine, 5-methylaminomethyluracil, methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl) uracil, 2,6-diaminopurine and biotinylated analogs, amongst others.

Examples of modified sugar moieties which may be used to modify nucleotides at any position on its structure include, but are not limited to, arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

Primers: Short nucleic acid molecules, such as a DNA oligonucleotide, for example sequences of at least 15 nucleotides, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, primers can be used to amplify a target nucleic acid molecule, wherein the sequence of the primer is specific for the target nucleic acid molecule, for example so that the primer will hybridize to the target nucleic acid molecule under very high stringency hybridization conditions. The specificity of a primer increases with its length. Thus, for example, a primer that includes 30 consecutive nucleotides will anneal to a target sequence with a higher specificity than a corresponding primer of only 15 nucleotides. Thus, to obtain greater specificity, probes and primers can be selected that include at least 15, 20, 25, 30, 35, 40, 45, 50 or more consecutive nucleotides.

In particular examples, a primer is at least 15 nucleotides in length, such as at least 15 contiguous nucleotides complementary to a target nucleic acid molecule. Particular lengths of primers that can be used to practice the methods of the present disclosure, include primers having at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 45, at least 50, or more contiguous nucleotides complementary to the target nucleic acid molecule to be amplified, such as a primer of 15-60 nucleotides, 15-50 nucleotides, or 15-30 nucleotides.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction. PCR primer pairs can be derived from a known sequence, for example, by using computer programs intended for that purpose such as Primer (Version 0.5, © 1991, Whitehead Institute for Biomedical Research, Cambridge, Mass.).

Methods for preparing and using primers are described in, for example, Sambrook et al. (1989) *Molecular Cloning: A Laboratory Manual*, Cold Spring Harbor, New York; Ausubel et al. (1987) *Current Protocols in Molecular Biology*, Greene Publ. Assoc. & Wiley-Intersciences. In one example, a primer includes a label.

Probe: A probe comprises an isolated nucleic acid capable of hybridizing to a target nucleic acid (such as a pathogen nucleic acid). A detectable label or reporter molecule can be attached to a probe. Typical labels include radioactive isotopes, enzyme substrates, co-factors, ligands, chemiluminescent or fluorescent agents, haptens, and enzymes.

Methods for labeling and guidance in the choice of labels appropriate for various purposes are discussed, for example, in Sambrook et al., *Molecular Cloning: A Laboratory Manual*, Cold Spring Harbor Laboratory Press (1989) and Ausubel et al., *Current Protocols in Molecular Biology*, Greene Publishing Associates and Wiley-Intersciences (1987).

In a particular example, a probe includes at least one fluorophore, such as an acceptor fluorophore or donor fluorophore. For example, a fluorophore can be attached at the 5'- or 3'-end of the probe. In specific examples, the fluorophore is attached to the base at the 5'-end of the probe, the base at its 3'-end, the phosphate group at its 5'-end or a modified base, such as a T internal to the probe.

Probes are generally about 15 nucleotides in length to about 160 nucleotides in length, such as 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 contiguous nucleotides complementary to the target nucleic acid molecule, such as 50-140 nucleotides, 75-150 nucleotides, 60-70 nucleotides, 30-130 nucleotides, 20-60 nucleotides, 20-50 nucleotides, 20-40 nucleotides, 20-30 nucleotides, or 40 to 60 nucleotides.

Polymerizing agent: A compound capable of reacting monomer molecules (such as nucleotides) together in a chemical reaction to form linear chains or a three-dimensional network of polymer chains. A particular example of a polymerizing agent is polymerase, an enzyme which catalyzes the 5' to 3' elongation of a primer strand complementary to a nucleic acid template. Examples of polymerases that can be used to amplify a nucleic acid molecule include, but are not limited to the E. coli DNA polymerase I, specifically the Klenow fragment which has 3' to 5' exonuclease activity, Taq polymerase, reverse transcriptase (such as HIV-1 RT), E. coli RNA polymerase, and wheat germ RNA polymerase II.

The choice of polymerase is dependent on the nucleic acid to be amplified. If the template is a single-stranded DNA molecule, a DNA-directed DNA or RNA polymerase can be used; if the template is a single-stranded RNA molecule, then a reverse transcriptase (such as an RNA-directed DNA polymerase) can be used.

Quantitating a nucleic acid molecule: Determining or measuring a quantity (such as a relative quantity) of nucleic acid molecule present, such as the number of amplicons or the number of nucleic acid molecules present in a sample. In particular examples, it is determining the relative amount or actual number of nucleic acid molecules present in a sample.

Quenching of fluorescence: A reduction of fluorescence. For example, quenching of a fluorophore's fluorescence occurs when a quencher molecule (such as fluorescence quenchers listed above) is present in sufficient proximity to the fluorophore that it reduces the fluorescence signal.

Figure 2:
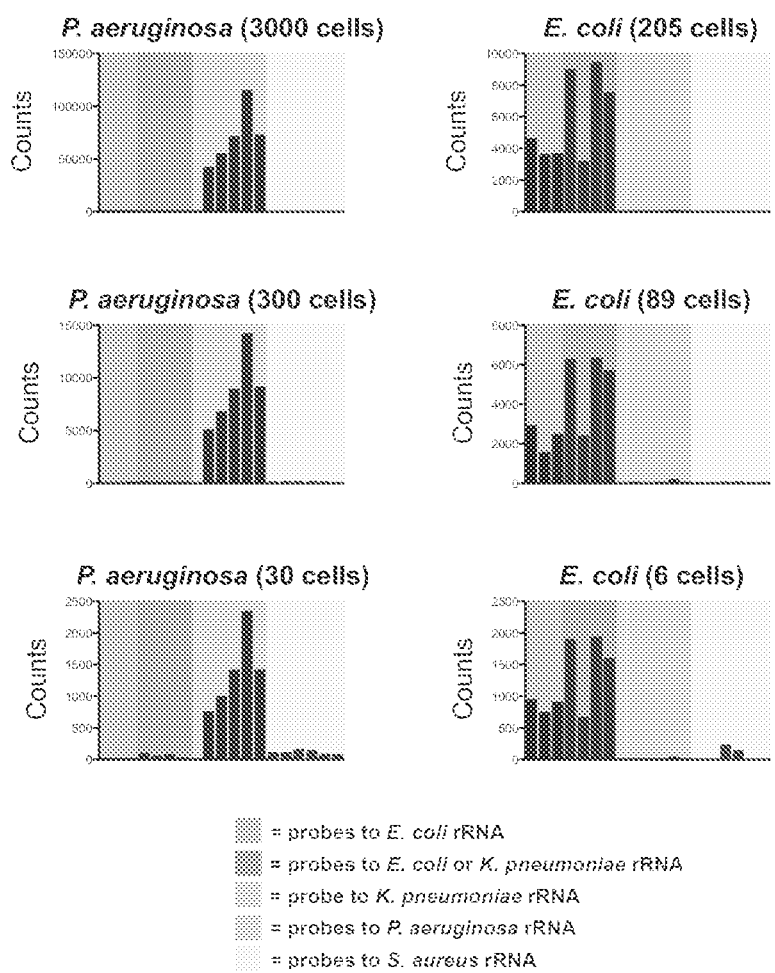
FIG. 2 are graphs of the results of the probes sets against low concentrations of two major clinical pathogens: *Pseudomonas aeruginosa* and *Escherichia coli*.

Real-time PCR: A method for detecting and measuring products generated during each cycle of a PCR, which are proportionate to the amount of template nucleic acid prior to the start of PCR. The information obtained, such as an amplification curve, can be used to determine the presence of a target nucleic acid and/or quantitate the initial amounts of a target nucleic acid sequence. In some examples, real time PCR is real time reverse transcriptase PCR (rt RT-PCR). In some examples, the amount of amplified target nucleic acid (is detected using a labeled probe, such as a probe labeled with a fluorophore, for example a TAQMAN® probe. In this example, the increase in fluorescence emission is measured in real time, during the course of the RT-PCR. This increase in fluorescence emission is directly related to the increase in target nucleic acid amplification. In some examples the change in fluorescence (dRn) is calculated using the equation $dRn=Rn^+-Rn^-$, with $Rn^+$ being the fluorescence emission of the product at each time point and $Rn^-$ being the fluorescence emission of the baseline. The dRn values are plotted against cycle number, resulting in amplification plots for each sample as illustrated in FIG. 2. With reference to FIG. 2, the threshold value (Ct) is the PCR cycle number at which the fluorescence emission (dRn) exceeds a chosen threshold, which is typically 10 times the standard deviation of the baseline (this threshold level can, however, be changed manually if desired).

Ribosomal Ribonucleic Acid (rRNA): Ribosomal ribonucleic acid (RNA) is a molecule in cells that forms part of the protein-synthesizing organelle known as a ribosome and that is exported to the cytoplasm to help translate the information in messenger RNA (mRNA) into protein. The three major types of RNA that occur in cells include rRNA, mRNA, and transfer RNA (tRNA).

The rRNAs form extensive secondary structures and play an active role in recognizing conserved portions of mRNAs and tRNAs. In eukaryotes (organisms that possess a clearly defined nucleus), anywhere from 50 to 5,000 sets of rRNA genes and as many as 10 million ribosomes, may be present in a single cell. In contrast, prokaryotes (organisms that lack a nucleus) generally have fewer sets of rRNA genes and ribosomes per cell. For example, in the bacterium *Escherichia coli*, seven copies of the rRNA genes synthesize about 15,000 ribosomes per cell.

Sample: A sample, such as a biological sample, that includes biological materials (such as nucleic acid and proteins, for example, double-stranded nucleic acid binding proteins) obtained from an organism or a part thereof, such as a plant, animal, bacteria, and the like. In particular embodiments, the biological sample is obtained from an animal subject, such as a human subject. A biological sample is any solid or fluid sample obtained from, excreted by or secreted by any living organism, including without limitation, single celled organisms, such as bacteria, yeast, protozoans, and amoebas among others, multicellular organisms (such as plants or animals, including samples from a healthy or apparently healthy human subject or a human patient affected by a condition or disease to be diagnosed or investigated). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease, such as rheumatoid arthritis, osteoarthritis, gout or septic arthritis). A sample can also be a sample obtained from any organ or tissue (including a biopsy or autopsy specimen, such as a tumor biopsy) or can include a cell (whether a primary cell or cultured cell) or medium conditioned by any cell, tissue or organ.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Homologs or orthologs of nucleic acid or amino acid sequences possess a relatively high degree of sequence identity/similarity when aligned using standard methods. Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations. The NCBI Basic Local Alignment Search Tool (BLAST) (Altschul et al., *J. Mol. Biol.* 215: 403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (i.e., 15±20*100=75).

One indication that two nucleic acid molecules are closely related is that the two molecules hybridize to each other under stringent conditions. Stringent conditions are sequence-dependent and are different under different environmental parameters.

The nucleic acid probes and primers disclosed herein are not limited to the exact sequences shown, as those skilled in the art will appreciate that changes can be made to a sequence, and not substantially affect the ability of the probe or primer to function as desired. For example, sequences having at least 80%, at least 90%, at least 95%, at least 96%, at least 97%, at least 98%, or at least 99% sequence identity to any of SEQ ID NOS: 1-106 are provided herein. One of skill in the art will appreciate that these sequence identity ranges are provided for guidance only; it is possible that probes and primer can be used that fall outside these ranges.

Signal: A detectable change or impulse in a physical property that provides information. In the context of the disclosed methods, examples include electromagnetic signals such as light, for example light of a particular quantity or wavelength. In certain examples the signal is the disappearance of a physical event, such as quenching of light.

TAQMAN® probes: A linear oligonucleotide probe with a 5' reporter fluorophore such as 6-carboxyfluorescein (FAM) and a 3' quencher fluorophore, such as BLACK-HOLE QUENCHER™ 1 (BHQ™ 1). In the intact TAQMAN® probe, energy is transferred (via FRET) from the short-wavelength fluorophore to the long-wavelength fluorophore on the other end, quenching the short-wavelength fluorescence. After hybridization, the probe is susceptible to degradation by the endonuclease activity of a processing Taq polymerase. Upon degradation, FRET is interrupted, increasing the fluorescence from the short-wavelength fluorophore and decreasing fluorescence from the long-wavelength fluorophore.

Target ribonucleic acid molecule: A ribonucleic acid molecule whose detection, quantitation, qualitative detection, or a combination thereof, is intended. The ribonucleic acid molecule need not be in a purified form. Various other ribonucleic acid molecules can also be present with the target ribonucleic acid molecule. For example, the target ribonucleic acid molecule can be a specific ribonucleic acid molecule. Purification or isolation of the target ribonucleic acid molecule, if needed, can be conducted by methods known to those in the art, such as by using a commercially available purification kit or the like. In one example, a target ribonucleic molecule is a pathogen nucleic acid sequence.

Tissue: A plurality of functionally related cells. A tissue can be a suspension, a semi-solid, or solid. Tissue includes cells collected from a subject such as blood, cervix, uterus, lymph nodes, breast, skin, and other organs.

Under conditions that permit binding: A phrase used to describe any environment that permits the desired activity, for example conditions under which two or more molecules, such as nucleic acid molecules and/or protein molecules, can bind. In some embodiments, conditions that permit binding are highly denaturing conditions.

Suitable methods and materials for the practice or testing of this disclosure are described below. Such methods and materials are illustrative only and are not intended to be limiting. Other methods and materials similar or equivalent to those described herein can be used. For example, conventional methods well known in the art to which this disclosure pertains are described in various general and more specific references, including, for example, Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999. In addition, the materials, methods, and examples are illustrative only and not intended to be limiting.

II. Overview of Several Embodiments

The present disclosure relates to methods of detecting the presence of a pathogen in a sample, such as a biological sample obtained from a subject. Disclosed is a hybridization-based method to identify bacterial species based on annealing to the ribosomal RNA present in a sample. This disclosure fulfills a need or needs not yet satisfied by the methods previously or presently available. Particular embodiments disclosed herein describe an array of probes that will identify and distinguish bacterial species within a single hybridization test allowing for recognition of many different bacteria by targeting ribosomal RNA transcripts. The present methods allow the detection of pathogens and distinguishing between two or more species of one or more organisms, e.g., bacteria, yeast, and fungi or a combination thereof, in a biological sample, by detecting the hybridization between the sample containing ribosomal ribonucleic acid (rRNA) and one or more antisense probes, wherein the probes contain at least one detectable probe that is specific for a target rRNA sequence of the species to be tested.

Disclosed herein are methods for distinguishing between two or more species of one or more organisms in a sample. The methods are also amenable to detecting one or more species of one or more organisms in a sample.

The methods comprise, for example, contacting a sample comprising ribosomal ribonucleic acid (rRNA), such as a sample obtained from a subject, such as a human subject, with a set of antisense probes. The set of probes comprises at least one detectable probe that is specific for a target rRNA sequence of each species to be tested, wherein the individual probes specific for each species have about 85% or less sequence identity to the probes for the other species, such as less than about 75%, less than about 70%, or even less than about 50% sequence identity to the probes for the other species. The method further comprises detecting hybridization between one or more of the probes and the rRNA, thereby distinguishing between two or more species in a sample. In certain example embodiments, the individual probes specific for each species have about 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60% or less sequence identity to the probes for the other species.

Hybridization between one or more of the probes and the rRNA is detected, thereby distinguishing between two or more species in a sample. In some embodiments, detecting hybridization between the probe indicates the presence of the species in the sample, and can indicate that the subject from which, the sample was obtained is infected with the organism. In some embodiments, the organisms include, or consist of, one or more microorganisms, for example, bacteria, yeast, and fungi or a combination thereof. In some examples the one or more microorganism include one or more human pathogens. In specific examples, the one or more microorganism includes one or more of *Escherichia coli*, *Klebsiella pneumoniae*, *Pseudomonas aeruginosa*, *Acinetobacter baumannii*, *Candida albicans*, *Enterobacter cloacae*, *Enterococcus faecalis*, *Enterococcus faecium*, *Proteus mirabilis*, *Streptococcus agalactiae*, *Stenotrophomonas maltophilia*, or *Staphylococcus aureus*.

By way of example the sequences of annotated 16S rRNA-encoding genes are extracted from the NCBI database of fully sequenced bacterial genomes. 16S rRNA sequences derived from all strains of interest are examined to identify conserved regions among strains of the same species but significantly divergent among different species. These regions are then targeted for hybridization-based detection, for example using Nanostring's method of two DNA oligonucleotides that bind to adjacent 50-nucleotide stretches of RNA. When the target transcript is present in a lysate, it links a biotinylated DNA oligo (the "capture probe") to an adjacent fluorescently labeled DNA oligo (the "reporter probe").

In some embodiments, the target rRNA sequence of each species to be tested comprise at least 2 of the nucleic acid sequences set forth as SEQ ID NO: 107-159, wherein each species specific probe in set of antisense probes specifically binds to the nucleic acid sequences set forth as SEQ ID NOs: 107-159. The organisms corresponding to each of SEQ ID NOs: 107-159 are shown in Examples below.

In specific embodiments, the set of antisense probes includes one or more probes to *Acinetobacter baumanniii*, wherein the one or more probes is at least 95% identical, such as at least 96%, at least 97%, at least 98%, at least 99%, or even 100% identical to the nucleic acid sequence set forth as SEQ ID NO: 1, SEQ ID NO: 2, SEQ ID NO: 54, or SEQ ID NO: 55.

In specific embodiments, the set of antisense probes includes one or more probes to *Candida albicans*, wherein the one or more probes is at least 95% identical, such as at least 96%, at least 97%, at least 98%, at least 99%, or even 100% identical to the nucleic acid sequence set forth as SEQ ID NO: 3, SEQ ID NO: 4, SEQ ID NO: 56, or SEQ ID NO: 57.

In specific embodiments, the set of antisense probes includes one or more probes to *Enterobacter cloacae*, wherein the one or more probes is at least 95% identical, such as at least 96%, at least 97%, at least 98%, at least 99%, or even 100% identical to the nucleic acid sequence set forth as SEQ ID NO: 5 or SEQ ID NO: 58.

In specific embodiments, the set of antisense probes includes one or more probes to *Escherichia coli*, wherein the one or more probes is at least 95% identical, such as at least 96%, at least 97%, at least 98%, at least 99%, or even 100% identical to the nucleic acid sequence set forth as SEQ ID NO: 8, SEQ ID NO: 9, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 59, SEQ ID NO: 60, or SEQ ID NO: 64, SEQ ID NO: 65, SEQ ID NO: 66, SEQ ID NO: 67, SEQ ID NO: 68, SEQ ID NO: 69, SEQ ID NO: 70, or SEQ ID NO: 71.

In specific embodiments, the set of antisense probes includes one or more probes to *Enterococcus faecalis*, wherein the one or more probes is at least 95% identical, such as at least 96%, at least 97%, at least 98%, at least 99%, or even 100% identical to the nucleic acid sequence set forth as SEQ ID NO: 8 or SEQ ID NO: 61.

In specific embodiments, the set of antisense probes includes one or more probes to *Enterococcus faecium*, wherein the one or more probes is at least 95% identical, such as at least 96%, at least 97%, at least 98%, at least 99%, or even 100% identical to the nucleic acid sequence set forth as SEQ ID NO: 9, SEQ ID NO: 10, SEQ ID NO: 62, or SEQ ID NO: 63.

In specific embodiments, the set of antisense probes includes one or more probes to one or more probes to *Klebsiella pneumoniae*, wherein the one or more probes is at least 95% identical, such as at least 96%, at least 97%, at least 98%, at least 99%, or even 100% identical to the nucleic acid sequence set forth as SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 72, SEQ ID NO: 73, SEQ ID NO: 74, SEQ ID NO: 75, SEQ ID NO: 76, or SEQ ID NO: 77, or SEQ ID NO: 78.

In specific embodiments, the set of antisense probes includes one or more probes to one or more probes to *Pseudomonas aeruginosa*, wherein the one or more probes is at least 95% identical, such as at least 96%, at least 97%, at least 98%, at least 99%, or even 100% identical to the nucleic acid sequence set forth as SEQ ID NO: 26, SEQ ID NO: 28, SEQ ID NO: 29, SEQ ID NO: 30, SEQ ID NO: 31, SEQ ID NO: 32, or SEQ ID NO: 33, SEQ ID NO: 34, SEQ ID NO: 79, SEQ ID NO: 81, SEQ ID NO: 82, SEQ ID NO: 83, SEQ ID NO: 84, SEQ ID NO: 85, or SEQ ID NO: 86, or SEQ ID NO: 87.

In specific embodiments, the set of antisense probes includes one or more probes to *Proteus mirabilis*, wherein the one or more probes is at least 95% identical, such as at least 96%, at least 97%, at least 98%, at least 99%, or even 100% identical to the nucleic acid sequence set forth as SEQ ID NO: 27, or SEQ ID NO: 80.

In specific embodiments, the set of antisense probes includes one or more probes to *Staphylococcus* sp, wherein the one or more probes is at least 95% identical, such as at least 96%, at least 97%, at least 98%, at least 99%, or even 100% identical to the nucleic acid sequence set forth as SEQ ID NO: 35, SEQ ID NO: 36, SEQ ID NO: 88, or SEQ ID NO: 89.

In specific embodiments, the set of antisense probes includes one or more probes to *S. agalactiae*, wherein the one or more probes is at least 95% identical, such as at least 96%, at least 97%, at least 98%, at least 99%, or even 100% identical to the nucleic acid sequence set forth as SEQ ID NO: 37, or SEQ ID NO: 38, SEQ ID NO: 90, or SEQ ID NO: 91.

In specific embodiments, the set of antisense probes includes one or more probes to *S. maltophilia*, wherein the one or more probes is at least 95% identical, such as at least 96%, at least 97%, at least 98%, at least 99%, or even 100% identical to the nucleic acid sequence set forth as SEQ ID NO: 40, or SEQ ID NO: 41, SEQ ID NO: 93, or SEQ ID NO: 94.

In specific embodiments, the set of antisense probes includes one or more probes to one or more probes to *Staphylococcus aureus*, wherein the one or more probes is at least 95% identical, such as at least 96%, at least 97%, at least 98%, at least 99%, or even 100% identical to the nucleic acid sequence set forth as SEQ ID NO: 40, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 93, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106.

In some embodiments of the disclosed methods, the sample is further contacted with a second set of antisense probes, wherein the second set of probes contains at least one second detectable probe that is specific for each species to be tested, and wherein the individual probes bind to substantially the same region of the rRNA as the first set of probes, but wherein the second set of probes do not overlap in sequence identity. In specific embodiments, the at least one second detectable probe that is specific for each species to be tested specifically bind the nucleic acid sequences set forth as one of SEQ ID NOs: 107-159, such as a nucleic acid sequence at least 95% identical, such as at least 96%, at least 97%, at least 98%, at least 99%, or even 100% identical to the nucleic acid sequence set forth as any one of SEQ ID NOs. 1-106.

In particular embodiments, two molecular probes are added to a crude sample lysate containing rRNA molecules. A capture probe comprises 50 nucleotides complementary to a given rRNA molecule, and can be conjugated to biotin. A reporter probe comprises a different 50 nucleotides complementary to a different part of the same rRNA molecule, and can be conjugated to a reporter molecule, e.g., a fluorescent tag or quantum dot. Each reporter probe uniquely identifies a given rRNA molecule. The capture and reporter probes hybridize to their corresponding rRNA molecules within the lysate. Excess reporter is removed by bead purification that hybridizes to a handle on each oligomer, leaving only the hybridized rRNA complexes. The rRNA complexes can be captured and immobilized on a surface, e.g., a streptavidin-coated surface. An electric field can be applied to align the complexes all in the same direction on the surface before the surface is microscopically imaged.

In some embodiments, the technique employs a commercial RNA recognition technology known as NanoString, which has largely been applied to characterization of messenger RNA (mRNA) transcripts. The reporter probes can be counted to provide a quantitative measure of rRNA molecules. A commercially available nCounter™ Analysis System (NanoString, Seattle, Wash.) can be used in the procedure. It will be understood by those skilled in the art, that other systems may be used in the process.

Also disclosed are methods for detecting a bacterial species in a sample and/or classifying a bacterial strain in a sample. The methods include: contacting the sample with one or more detectable probes comprising a nucleic acid sequence capable of hybridizing to a bacterial ribosomal ribonucleic acid sequence set forth as one of SEQ ID NOs: 106-159; and detecting hybridization between the bacterial ribosomal ribonucleic acid and the probe, wherein the detection of the hybridization indicates the bacterial species is present. In some embodiments, the one or more detectable probes comprises the nucleic acid sequence set forth as any one of SEQ ID NO: 1-106. In some embodiments detection of a bacterial ribosomal ribonucleic acid sequence with one or more probes at least 95% identical to SEQ ID NO: 8, SEQ ID NO: 9, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 59, SEQ ID NO: 60, or SEQ ID NO: 64, SEQ ID NO: 65, SEQ ID NO: 66, SEQ ID NO: 67, SEQ ID NO: 68, SEQ ID NO: 69, SEQ ID NO: 70, or SEQ ID NO: 71 indicates the presence of *Escherichia coli*. In some embodiments detection of a bacterial ribosomal ribonucleic acid sequence with one or more probes at least 95% identical to SEQ ID NO: 1, SEQ ID NO: 2, SEQ ID NO: 54, or SEQ ID NO: 55 indicates the presence of *Acinetobacter baumanniii*. In some embodiments detection of a bacterial ribosomal ribonucleic acid sequence with one or more probes at least 95% identical to SEQ ID NO: 3, SEQ ID NO: 4, SEQ ID NO: 56, or SEQ ID NO: 57 indicates the presence of *Candida albicans*. In some embodiments detection of a bacterial ribosomal ribonucleic acid sequence with one or more probes at least 95% identical to SEQ ID NO: 5 or SEQ ID NO: 58 indicates the presence of *Enterobacter cloacae*. In some embodiments detection of a bacterial ribosomal ribonucleic acid sequence with one or more probes at least 95% identical to SEQ ID NO: 8 or SEQ ID NO: 61 indicates the presence of *Enterococcus faecalis*. In some embodiments detection of a bacterial ribosomal ribonucleic acid sequence with one or more probes at least 95% identical to SEQ ID NO: 9, SEQ ID NO: 10, SEQ ID NO: 62, or SEQ ID NO: 63 indicates the presence of *Enterococcus faecium*. In some embodiments detection of a bacterial ribosomal ribonucleic acid sequence with one or more probes at least 95% identical to SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 72, SEQ ID NO: 73, SEQ ID NO: 74, SEQ ID NO: 75, SEQ ID NO: 76, or SEQ ID NO: 77, or SEQ ID NO: 78 indicates the presence of *Klebsiella pneumonia*. In some embodiments detection of a bacterial ribosomal ribonucleic acid sequence with one or more probes at least 95% identical to SEQ ID NO: 26, SEQ ID NO: 28, SEQ ID NO: 29, SEQ ID NO: 30, SEQ ID NO: 31, SEQ ID NO: 32, or SEQ ID NO: 33, SEQ ID NO: 34, SEQ ID NO: 79, SEQ ID NO: 81, SEQ ID NO: 82, SEQ ID NO: 83, SEQ ID NO: 84, SEQ ID NO: 85, or SEQ ID NO: 86, or SEQ ID NO: 87 indicates the presence of *Pseudomonas aeruginosa*. In some embodiments detection of a bacterial ribosomal ribonucleic acid sequence with one or more probes at least 95% identical to SEQ ID NO: 27, or SEQ ID NO: 80 indicates the presence of *Proteus mirabilis*. In some embodiments detection of a bacterial ribosomal ribonucleic acid sequence with one or more probes at least 95% identical to SEQ ID NO: 35, SEQ ID NO: 36, SEQ ID NO: 88, or SEQ ID NO: 89 indicates the presence of *Staphylococcus* sp. In some embodiments detection of a bacterial ribosomal ribonucleic acid sequence with one or more probes at least 95% identical to SEQ ID NO: 37, or SEQ ID NO: 38, SEQ ID NO: 90, or SEQ ID NO: 91 indicates the presence of *S.* maltophilia. In some embodiments detection of a bacterial ribosomal ribonucleic acid sequence with one or more probes at least 95% identical to SEQ ID NO: 40, or SEQ ID NO: 41, SEQ ID NO: 93, or SEQ ID NO: 94 indicates the presence of S. agalactiae. In some embodiments detection of a bacterial ribosomal ribonucleic acid sequence with one or more probes at least 95% identical to SEQ ID NO: 40, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 93, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106 indicates the presence of Staphylococcus aureus.

In specific embodiments, the methods discriminate between an Escherichia coli ribosomal ribonucleic acid, a Klebsiella pneumoniae ribosomal ribonucleic acid, a Pseudomonas aeruginosa ribosomal ribonucleic acid, a Staphylococcus aureus ribosomal ribonucleic acid an Acinetobacter baumannii ribosomal ribonucleic acid, a Candida albicans ribosomal ribonucleic acid, a Enterobacter cloacae ribosomal ribonucleic acid, a Enterococcus faecalis ribosomal ribonucleic acid, a Enterococcus faecium ribosomal ribonucleic acid, a Proteus mirabilis ribosomal ribonucleic acid, or a Staphylococcus sp. ribosomal ribonucleic acid, a S. agalactiae ribosomal ribonucleic acid, or a S. maltophilia ribosomal ribonucleic acid. In such methods, the sample is contacted with a probe specific for n Escherichia coli ribosomal ribonucleic acid, a Klebsiella pneumoniae ribosomal ribonucleic acid, a Pseudomonas aeruginosa ribosomal ribonucleic acid, a Staphylococcus aureus ribosomal ribonucleic acid an Acinetobacter baumannii ribosomal ribonucleic acid, a Candida albicans ribosomal ribonucleic acid, a Enterobacter cloacae ribosomal ribonucleic acid, a Enterococcus faecalis ribosomal ribonucleic acid, a Enterococcus faecium ribosomal ribonucleic acid, a Proteus mirabilis ribosomal ribonucleic acid, or a Staphylococcus sp. ribosomal ribonucleic acid, a S. agalactiae ribosomal ribonucleic acid, or a S. maltophilia ribosomal ribonucleic acid, wherein: detection of the hybridization of a ribosomal ribonucleic acid molecule with the one or more probes The disclosed methods are particularly useful for diagnosing a species-specific bacterial infection in a subject suspected of having a bacterial infection such as an infection with Escherichia coli, Klebsiella pneumoniae, Pseudomonas aeruginosa, Acinetobacter baumannii, Candida albicans, Enterobacter cloacae, Enterococcus faecalis, Enterococcus faecium, Proteus mirabilis, Streptococcus agalactiae, Stenotrophomonas maltophilia or Staphylococcus aureus, or combination thereof. In some embodiments, the method further includes determining the at least one detectable probe that is specific for a target rRNA sequence of each species. The determination comprises, for example, determining shared rRNA sequences between members of each of the two or more species; determining divergent rRNA sequences between each of the two or more species, wherein the divergent rRNA sequences share about 85% or less sequence identity, such as less than about 80%, less than about 75%, less than about 70%, or even less than about 50% identity, to identify a target RNA sequence for each species; and, designing a probe for the target rRNA sequence of each species that specifically binds to the shared rRNA sequences between members of a given species, wherein the individual probes for are each species are about 85% or less identical, such as less than about less than about 75%, less than about 70%, or even less than about 50% identical. In certain example embodiments, the divergent rRNA sequences share about 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60% or less sequence identity. In certain example embodiments, the individual probes specific for each species have about 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60% or less sequence identity to the probes for the other species.

In some embodiments of the disclosed methods, determining the identity of a nucleic acid includes detection by nucleic acid hybridization. Nucleic acid hybridization involves providing a denatured probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus, specificity of hybridization is reduced at lower stringency. Conversely, at higher stringency (e.g., higher temperature or lower salt) successful hybridization requires fewer mismatches. One of skill in the art will appreciate that hybridization conditions can be designed to provide different degrees of stringency.

In general, there is a tradeoff between hybridization specificity (stringency) and signal intensity. Thus, in one embodiment, the wash is performed at the highest stringency that produces consistent results and that provides a signal intensity greater than approximately 10% of the background intensity. Thus, the hybridized array may be washed at successively higher stringency solutions and read between each wash. Analysis of the data sets thus produced will reveal a wash stringency above which the hybridization pattern is not appreciably altered and which provides adequate signal for the particular oligonucleotide probes of interest. In some examples, RNA is detected using Northern blotting or in situ hybridization (Parker & Barnes, Methods in Molecular Biology 106:247-283, 1999); RNase protection assays (Hod, Biotechniques 13:852-4, 1992); and PCR-based methods, such as reverse transcription polymerase chain reaction (RT-PCR) (Weis et al., Trends in Genetics 8:263-4, 1992).

Other methods for detecting and/or quantifying RNA are well known in the art. In some examples, the method utilizes RT-PCR. Generally, the first step in gene expression profiling by RT-PCR is the reverse transcription of the RNA template into cDNA, followed by its exponential amplification in a PCR reaction. Two commonly used reverse transcriptases are avian myeloblastosis virus reverse transcriptase (AMV-RT) and Moloney murine leukemia virus reverse transcriptase (MMLV-RT). The reverse transcription step is typically primed using specific primers, random hexamers, or oligo-dT primers, depending on the circumstances and the goal of expression profiling. For example, RNA can be reverse-transcribed using a GeneAmp® RNA PCR kit (Perkin Elmer, Calif.), following the manufacturer's instructions. The derived cDNA can then be used as a template in the subsequent PCR reaction or for DNA sequencing.

Although the PCR step can use a variety of thermostable DNA-dependent DNA polymerases, it typically employs the Taq DNA polymerase. TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendable by Taq DNA polymerase enzyme, and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments dissociate in solution, and signal from the released reporter dye is free from the quenching effect of the second fluorophore. One molecule of reporter dye is liberated for each new molecule synthesized, and detection of the unquenched reporter dye provides the basis for quantitative interpretation of the data.

A variation of RT-PCR is real time quantitative RT-PCR, which measures PCR product accumulation through a dual-labeled fluorogenic probe (e.g., TaqMan® probe). Real time PCR is compatible both with quantitative competitive PCR, where internal competitor for each target sequence is used for normalization, and with quantitative comparative PCR using a normalization gene contained within the sample, or a housekeeping gene for RT-PCR (see Heid et al., *Genome Research* 6:986-994, 1996). Quantitative PCR is also described in U.S. Pat. No. 5,538,848. Related probes and quantitative amplification procedures are described in U.S. Pat. Nos. 5,716,784 and 5,723,591. Instruments for carrying out quantitative PCR in microtiter plates are available from PE Applied Biosystems (Foster City, Calif.).

TaqMan® RT-PCR can be performed using commercially available equipment, such as, for example, ABI PRISM 7700® Sequence Detection System® (Perkin-Elmer-Applied Biosystems, Foster City, Calif.), or Lightcycler® (Roche Molecular Biochemicals, Mannheim, Germany). In one example, the 5' nuclease procedure is run on a real-time quantitative PCR device such as the ABI PRISM 7700® Sequence Detection System®.

In some examples, 5'-nuclease assay data are initially expressed as Ct, or the threshold cycle. As discussed above, fluorescence values are recorded during every cycle and represent the amount of product amplified to that point in the amplification reaction. The point when the fluorescent signal is first recorded as statistically significant is the threshold cycle (Ct).

In some examples, nucleic acids are identified or confirmed using the microarray technique.

Detectable labels suitable for use include any composition detectable by spectroscopic, photochemical, biochemical, immunochemical, electrical, optical or chemical means. Useful labels include biotin for staining with labeled streptavidin conjugate, magnetic beads (for example DYNABEADS™), fluorescent dyes (for example, fluorescein, Texas red, rhodamine, green fluorescent protein, and the like), radiolabels (for example, $^3$H, $^{125}$I, $^{35}$S, $^{14}$C, or $^{32}$P), enzymes (for example, horseradish peroxidase, alkaline phosphatase and others commonly used in an ELISA), and colorimetric labels such as colloidal gold or colored glass or plastic (for example, polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241. In some embodiments, a disclosed probe is labeled. I some embodiments, the probes are differentially labeled, for example with different reports, so that the probes may be used in multiplex assay. In specific embodiment the probe is radiolabeled, fluorescently-labeled, biotin-labeled, enzymatically-labeled, or chemically-labeled. In some embodiments, the label comprises a capture moiety, such as biotin.

In some embodiments, the probe is attached to a solid surface.

Means of detecting such labels are also well known. Thus, for example, radiolabels may be detected using photographic film or scintillation counters. Fluorescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

The label may be added to the target (sample) nucleic acid(s) prior to, or after, the hybridization. So-called "direct labels" are detectable labels that are directly attached to or incorporated into the target (sample) nucleic acid prior to hybridization. In contrast, so-called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected (see *Laboratory Techniques in Biochemistry and Molecular Biology*, Vol. 24: *Hybridization With Nucleic Acid Probes*, P. Tijssen, ed. Elsevier, N. Y., 1993).

Appropriate samples for use in the methods disclosed herein include any conventional biological sample obtained from an organism or a part thereof, such as a plant, animal, bacteria, and the like. In particular embodiments, the biological sample is obtained from an animal subject, such as a human subject. A biological sample is any solid or fluid sample obtained from, excreted by or secreted by any living organism, including, without limitation, single celled organisms, such as bacteria, yeast, protozoans, and amoebas among others, multicellular organisms (such as plants or animals, including samples from a healthy or apparently healthy human subject or a human patient affected by a condition or disease to be diagnosed or investigated, such as an infection with a pathogenic microorganism, such as a pathogenic). For example, a biological sample can be a biological fluid obtained from, for example, blood, plasma, serum, urine, bile, ascites, saliva, cerebrospinal fluid, aqueous or vitreous humor, or any bodily secretion, a transudate, an exudate (for example, fluid obtained from an abscess or any other site of infection or inflammation), or fluid obtained from a joint (for example, a normal joint or a joint affected by disease, such as rheumatoid arthritis, osteoarthritis, gout or septic arthritis).

A sample can also be a sample obtained from any organ or tissue (including a biopsy or autopsy specimen, such as a tumor biopsy) or can include a cell (whether a primary cell or cultured cell) or medium conditioned by any cell, tissue or organ. Exemplary samples include, without limitation, cells, cell lysates, blood smears, cytocentrifuge preparations, cytology smears, bodily fluids (e.g., blood, plasma, serum, saliva, sputum, urine, bronchoalveolar lavage, semen, etc.), tissue biopsies (e.g., tumor biopsies), fine-needle aspirates, and/or tissue sections (e.g., cryostat tissue sections and/or paraffin-embedded tissue sections). In other examples, the sample includes circulating tumor cells (which can be identified by cell surface markers). In particular examples, samples are used directly (e.g., fresh or frozen), or can be manipulated prior to use, for example, by fixation (e.g., using formalin) and/or embedding in wax (such as formalin-fixed paraffin-embedded (FFPE) tissue samples). It will appreciated that any method of obtaining tissue from a subject can be utilized, and that the selection of the method used will depend upon various factors such as the type of tissue, age of the subject, or procedures available to the practitioner. Standard techniques for acquisition of such samples are available. See, for example Schluger et al., *J. Exp. Med.* 176:1327-33 (1992); Bigby et al., *Am. Rev. Respir. Dis.* 133:515-18 (1986); Kovacs et al., *NEJM* 318: 589-93 (1988); and Ognibene et al., *Am. Rev. Respir. Dis.* 129:929-32 (1984).

In another embodiment, a detectable probe that is specific for a target rRNA sequence of a species is determined, wherein the determination comprises: determining shared rRNA sequences between members of each of the two or more species; determining divergent rRNA sequences between each of the two or more species, wherein the divergent rRNA sequences share about 85% or less sequence identity, to identify a target RNA sequence for each species; and, designing a probe for the target rRNA sequence of each species that specifically binds to the shared rRNA sequences between members of a given species, wherein the individual probes for are each species are about 85% identical. In certain example embodiments, the divergent rRNA sequences share about 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60% or less sequence identity. In certain example embodiments, the individual probes specific for each species have about 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60% or less sequence identity to the probes for the other species.

Several embodiments of the present disclosure involve the use of procedures and approaches known in the art to successfully fractionate clinical blood samples. See, e.g. the procedure described in Han Wei Hou et al., *Microfluidic Devices for Blood Fractionation*, Micromachines 2011, 2, 319-343; Ali Asgar S. Bhagat et al., *Dean Flow Fractionation (DFF) Isolation of Circulating Tumor Cells (CTCs) from Blood*, 15th International Conference on Miniaturized Systems for Chemistry and Life Sciences, Oct. 2-6, 2011, Seattle, Wash.; and International Patent Publication No. WO2011109762, the disclosures of which are herein incorporated by reference in their entirety.

Further, several embodiments of the present disclosure involve the use of procedures and approaches known in the art to successfully isolate pathogens from whole blood using spiral microchannel, as described in Han Wei Hou et al., Pathogen Isolation from Whole Blood Using Spiral Microchannel, Case No. 15995JR, Massachusetts Institute of Technology, manuscript in preparation, the disclosure of which is herein incorporated by reference in its entirety.

In some embodiments, a method of diagnosing a species-specific bacterial infection in a subject suspected of having a bacterial infection is described as obtaining a sample comprising bacterial ribosomal ribonucleic acid from the subject; contacting the sample with one or more of the probes described, and detecting hybridization between the bacterial ribosomal ribonucleic acid sequence present in the sample and the probe, wherein the detection of hybridization indicates that the subject is infected with *Escherichia coli, Klebsiella pneumoniae, Pseudomonas aeruginosa, Staphylococcus aureus, Acinetobacter baumannii, Candida albicans, Enterobacter cloacae, Enterococcus faecalis, Enterococcus faecium, Proteus mirabilis, Staphylococcus agalactiae,* or *Staphylococcus maltophilia* or a combination thereof Probes Disclosed nucleic acid probes for the detection of and discrimination between organisms. Typically the probes are between 15 and 160 nucleotides in length, such 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160 contiguous nucleotides complementary to the target nucleic acid molecule, such as 50-140 nucleotides, 75-150 nucleotides, 60-70 nucleotides, 30-130 nucleotides, 20-60 nucleotides, 20-50 nucleotides, 20-40 nucleotides, 20-30 nucleotides, or 40-60 nucleotides and capable of hybridizing to a rRNA sequence. In some embodiments, the probes are specific for a target rRNA sequence from an organism at the exclusion of other organisms. The probes can be selected by determining at least one detectable probe that is specific for a target rRNA sequence of each species, the determination comprising determining shared rRNA sequences between members of each of the two or more species; determining divergent rRNA sequences between each of the two or more species of the one or more organisms, wherein the divergent rRNA sequences share about 85% or less sequence identity, such as less than about 80%, less than about 75%, less than about 70%, or even less than about 50% identity, to identify a target RNA sequence for each species; and, designing a probe for the target rRNA sequence of each species that specifically binds to the shared rRNA sequences between members of a given species, wherein the individual probes for are each species are about 85% or less identical, such as less than about less than about 75%, less than about 70%, or even less than about 50% identical. In some embodiment, the probes are RNA, DNA or a combination thereof. In certain example embodiments, the divergent rRNA sequences share about 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60% or less sequence identity. In certain example embodiments, the individual probes specific for each species have about 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60% or less sequence identity to the probes for the other species.

In some embodiments, the probe is for the detection of a bacterial species and is capable of hybridizing to a bacterial species rRNA sequence, the probe comprising a nucleic acid sequence at least 95% identical to the nucleic acid sequence set forth as set forth as bacterial species rRNA sequence, the probe comprising a nucleic acid sequence at least 95% identical to the nucleic acid sequence set forth as set forth as one of SEQ ID NO: 1-106.

In specific embodiments the probe specific for *Acinetobacter baumannii* is at least 95% identical, such as at least 96%, at least 97%, at least 98%, at least 99%, or even 100% identical to the nucleic acid sequence set forth as SEQ ID NO: 1, SEQ ID NO: 2, SEQ ID NO: 54, or SEQ ID NO: 55.

In specific embodiments the probe specific for *Escherichia coli* is at least 95% identical, such as at least 96%, at least 97%, at least 98%, at least 99%, or even 100% identical to the nucleic acid sequence set forth as SEQ ID NO: 8, SEQ ID NO: 9, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 59, SEQ ID NO: 60, or SEQ ID NO: 64, SEQ ID NO: 65, SEQ ID NO: 66, SEQ ID NO: 67, SEQ ID NO: 68, SEQ ID NO: 69, SEQ ID NO: 70, or SEQ ID NO: 71.

In specific embodiments the probe specific for *Enterococcus faecalis* is at least 95% identical, such as at least 95% identical, such as at least 96%, at least 97%, at least 98%, at least 99%, or even 100% identical to the nucleic acid sequence set forth as SEQ ID NO: 8 or SEQ ID NO: 61.

In specific embodiments the probe specific for *Enterococcus faecium* is at least 95% identical, such as at least 96%, at least 97%, at least 98%, at least 99%, or even 100% identical to the nucleic acid sequence set forth as SEQ ID NO: 9, SEQ ID NO: 10, SEQ ID NO: 62, or SEQ ID NO: 63.

In specific embodiments the probe specific for *Candida albicans* is at least 95% identical, such as at least 96%, at least 97%, at least 98%, at least 99%, or even 100% identical to the nucleic acid sequence set forth as SEQ ID NO: 3, SEQ ID NO: 4, SEQ ID NO: 56, or SEQ ID NO: 57.

In specific embodiments the probe specific for *Klebsiella pneumoniae* is at least 95% identical, such as at least 96%, at least 97%, at least 98%, at least 99%, or even 100% identical to the nucleic acid sequence set forth as SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 72, SEQ ID NO: 73, SEQ ID NO: 74, SEQ ID NO: 75, SEQ ID NO: 76, or SEQ ID NO: 77, or SEQ ID NO: 78.

In specific embodiments the probe specific for *Pseudomonas aeruginosa* is at least 95% identical, such as at least 96%, at least 97%, at least 98%, at least 99%, or even 100% identical to the nucleic acid sequence set forth as SEQ ID NO: 26, SEQ ID NO: 28, SEQ ID NO: 29, SEQ ID NO: 30, SEQ ID NO: 31, SEQ ID NO: 32, or SEQ ID NO: 33, SEQ ID NO: 34, SEQ ID NO: 79, SEQ ID NO: 81, SEQ ID NO: 82, SEQ ID NO: 83, SEQ ID NO: 84, SEQ ID NO: 85, or SEQ ID NO: 86, or SEQ ID NO: 87.

In specific embodiments the probe specific for *Proteus mirabilis* is at least 95% identical, such as at least 96%, at least 97%, at least 98%, at least 99%, or even 100% identical to the nucleic acid sequence set forth as SEQ ID NO: 27, or SEQ ID NO: 80.

In specific embodiments the probe specific for *Staphylococcus sp* is at least 95% identical, such as at least 96%, at least 97%, at least 98%, at least 99%, or even 100% identical to the nucleic acid sequence set forth as SEQ ID NO: 35, SEQ ID NO: 36, SEQ ID NO: 88, or SEQ ID NO: 89.

In specific embodiments the probe specific for *S. agalactiae* is at least 95% identical, such as at least 96%, at least 97%, at least 98%, at least 99%, or even 100% identical to the nucleic acid sequence set forth as SEQ ID NO: 37, or SEQ ID NO: 38, SEQ ID NO: 90, or SEQ ID NO: 91.

In specific embodiments the probe specific for *S. maltophilia* is at least 95% identical, such as at least 96%, at least 97%, at least 98%, at least 99%, or even 100% identical to the nucleic acid sequence set forth as SEQ ID NO: 40, SEQ ID NO: 41, SEQ ID NO: 93, or SEQ ID NO: 94.

In specific embodiments the probe specific for *Staphylococcus aureus* is at least 95% identical, such as at least 96%, at least 97%, at least 98%, at least 99%, or even 100% identical to the nucleic acid sequence set forth as SEQ ID NO: 40, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 93, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106.

Also disclosed are sets of probes, including at least one probe disclosed herein.

Probes capable of hybridizing to and detecting the presence of ribosomal ribonucleic acids are specifically disclosed. The disclosed probes are between 50 and 100 nucleotides in length, and are capable of hybridizing to the rRNA of microorganisms. In several embodiments, a probe is capable of hybridizing under stringent conditions (such as high stringency, or very high stringency conditions) to a bacterial rRNA sequence set forth as one of SEQ ID NO: 107-159.

In several embodiments, a probe capable of hybridizing to a ribonucleic acid molecule contains a nucleic acid sequence that is at least 95% identical, such as at least 96%, at least 97%, at least 98%, at least 99%, or even 100% identical to nucleic acid sequence set forth as one of SEQ ID NOs: 1-106. In several embodiments, a probe capable of hybridizing to a ribonucleic acid molecule consists essentially of a nucleic acid sequence set forth as one of SEQ ID NOs: 1-106.

In some embodiments, the probe is detectably labeled, either with an isotopic or non-isotopic label, alternatively the target ribonucleic acid (such as a bacterial ribonucleic acid) is labeled. Non-isotopic labels can, for instance, comprise a fluorescent or luminescent molecule, biotin, an enzyme or enzyme substrate or a chemical. Such labels are preferentially chosen such that the hybridization of the probe with target ribonucleic acid (such as a bacterial ribonucleic acid) can be detected. In some examples, the probe is labeled with a fluorophore. Examples of suitable fluorophore labels are given above. In some examples, the fluorophore is a donor fluorophore. In other examples, the fluorophore is an accepter fluorophore, such as a fluorescence quencher. In some examples, the probe includes both a donor fluorophore and an accepter fluorophore. Appropriate donor/acceptor fluorophore pairs can be selected using routine methods. In one example, the donor emission wavelength is one that can significantly excite the acceptor, thereby generating a detectable emission from the acceptor. In some examples, the probe is modified at the 3'-end to prevent extension of the probe by a polymerase. Detectable labels suitable for use include any composition detectable by spectroscopic, photochemical, biochemical, immunochemical, electrical, optical or chemical means. Useful labels include biotin for staining with labeled streptavidin conjugate, magnetic beads (for example DYNABEADS™), fluorescent dyes (for example, fluorescein, Texas red, rhodamine, green fluorescent protein, and the like), radiolabels (for example, $^3$H, $^{125}$I, $^{35}$S, $^{14}$C, or $^{32}$P), enzymes (for example, horseradish peroxidase, alkaline phosphatase and others commonly used in an ELISA), and colorimetric labels such as colloidal gold or colored glass or plastic (for example, polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241. In some embodiments, a disclosed probe is labeled. I some embodiments, the probes are differentially labeled, for example with different reports, so that the probes may be used in multiplex assay. In specific embodiment the probe is radiolabeled, fluorescently-labeled, biotin-labeled, enzymatically-labeled, or chemically-labeled. In some embodiments, the label comprises a capture moiety, such as biotin. In some embodiments, the probe is attached to a solid surface.

Although exemplary probes are provided in SEQ ID NOs: 1-106 one skilled in the art will appreciate that the probe sequence can be varied slightly by moving the probes a few nucleotides upstream or downstream from the nucleotide positions that they hybridize to on the target rRNA sequence, for example one of SEQ ID NOs. 107-159. For example, one of skill in the art will appreciate that by analyzing the sequences that variations of the probes and primers disclosed as SEQ ID NOs: 1-106 can be made by "sliding" the probes and/or primers a few nucleotides 5' or 3' from their positions.

Also provided by the present application are probes that include variations to the nucleotide sequences shown in any of SEQ ID NOS: 1-106, as long as such variations permit detection of the target rRNA. For example, a probe or primer can have at least 95% sequence identity such as at least 96%, at least 97%, at least 98%, at least 99% to a nucleic acid consisting of the sequence shown in any of SEQ ID NOs: 1-106. In such examples, the number of nucleotides does not change, but the nucleic acid sequence shown in any of SEQ ID NOs: 1-106 can vary at a few nucleotides, such as changes at 1, 2, 3, or 4 nucleotides.

The present application also provides probes and primers that are slightly longer or shorter than the nucleotide sequences shown in any of SEQ ID NOS: 1-106, as long as such deletions or additions permit detection of the desired target rRNA. For example, a probe can include a few nucleotide deletions or additions at the 5'- or 3'-end of the probe shown in any of SEQ ID NOs: 1-106, such as addition or deletion of 1, 2, 3, or 4 nucleotides from the 5'- or 3'-end, or combinations thereof (such as a deletion from one end and an addition to the other end). In such examples, the number of nucleotides changes.

Kits

The nucleic acid probes disclosed herein can be supplied in the form of a kit for use in detection of, and discrimination between, organisms, such as pathogenic microorganisms, including kits for any of the arrays described below. In such a kit, an appropriate amount of one or more of the nucleic acid probes is provided in one or more containers or held on a substrate. A nucleic acid probe may be provided suspended in an aqueous solution or as a freeze-dried or lyophilized powder, for instance. The container(s) in which the nucleic acid(s) are supplied can be any conventional container that is capable of holding the supplied form, for instance, microfuge tubes, ampoules, or bottles. The kits can include either labeled or unlabeled nucleic acid probes for use in detection of, and discrimination between, organisms, such as pathogenic microorganisms.

In some applications, one or more probes may be provided in pre-measured single use amounts in individual, typically disposable, tubes or equivalent containers. With such an arrangement, the sample to be tested can be added to the individual tubes.

The amount of nucleic acid probe supplied in the kit can be any appropriate amount, and may depend on the target market to which the product is directed. General guidelines for determining appropriate amounts may be found in Innis et al., Sambrook et al., and Ausubel et al.

Particular embodiments include a kit for detection of, and discrimination between, organisms, such as pathogenic microorganisms. Such a kit includes at least one probe specific for an rRNA and instructions. A kit may contain more than one different probe, such as 2, 3, 4, 5, 6, 7, 8, 9, 10, 11, 12, 13, 14, 15, 20, 25, 50, 100, or more probes. The instructions may include directions for obtaining a sample, processing the sample, preparing the probes, and/or contacting each probe with an aliquot of the sample. In certain embodiments, the kit includes an apparatus for separating the different probes, such as individual containers (for example, microtubules) or an array substrate (such as, a 96-well or 384-well microtiter plate). In particular embodiments, the kit includes prepackaged probes, such as probes suspended in suitable medium in individual containers (for example, individually sealed EPPENDORF® tubes) or the wells of an array substrate (for example, a 96-well microtiter plate sealed with a protective plastic film). In other particular embodiments, the kit includes equipment, reagents, and instructions for extracting and/or purifying nucleotides from a sample.

In some embodiments, a kit for detecting a bacterial ribosomal ribonucleic acid in a sample is described, wherein the kit contains a probe disclosed herein and instructions for hybridizing the probe to a bacterial ribosomal ribonucleic acid from a biological sample.

Organism Profiling Arrays

An array containing a plurality of heterogeneous probes for the detection of, and discrimination between, organisms, such as pathogenic microorganisms are disclosed. Such arrays may be used to rapidly detect, and discriminate between, organisms in a sample.

Arrays are arrangements of addressable locations on a substrate, with each address containing a nucleic acid, such as a probe. In some embodiments, each address corresponds to a single type or class of nucleic acid, such as a single probe, though a particular nucleic acid may be redundantly contained at multiple addresses. A "microarray" is a miniaturized array requiring microscopic examination for detection of hybridization. Larger "macroarrays" allow each address to be recognizable by the naked human eye and, in some embodiments, a hybridization signal is detectable without additional magnification. The addresses may be labeled, keyed to a separate guide, or otherwise identified by location.

In some embodiments, an organism profiling array is a collection of separate probes at the array addresses. The organism profiling array is then contacted with a sample suspected of containing rRNA from one or more organisms under conditions allowing hybridization between the probe and nucleic acids in the sample to occur. Any sample potentially containing, or even suspected of containing, rRNA from one or more organisms may be used, including nucleic acid extracts or lysates. A hybridization signal from an individual address on the array indicates that the probe hybridizes to a nucleotide within the sample. This system permits the simultaneous analysis of a sample by plural probes and yields information identifying the rRNA from one or more organisms contained within the sample. In alternative embodiments, the array contains rRNA from one or more organisms and the array is contacted with a sample containing a probe. In any such embodiment, either the probe or the rRNA acids may be labeled to facilitate detection of hybridization.

The nucleic acids may be added to an array substrate in dry or liquid form. Other compounds or substances may be added to the array as well, such as buffers, stabilizers, reagents for detecting hybridization signal, emulsifying agents, or preservatives.

In certain examples, the array includes one or more molecules or samples occurring on the array a plurality of times (twice or more) to provide an added feature to the array, such as redundant activity or to provide internal controls.

Within an array, each arrayed nucleic acid is addressable, such that its location may be reliably and consistently determined within the at least the two dimensions of the array surface. Thus, ordered arrays allow assignment of the location of each nucleic acid at the time it is placed within the array. Usually, an array map or key is provided to correlate each address with the appropriate nucleic acid. Ordered arrays are often arranged in a symmetrical grid pattern, but nucleic acids could be arranged in other patterns (for example, in radially distributed lines, a "spokes and wheel" pattern, or ordered clusters). Addressable arrays can be computer readable; a computer can be programmed to correlate a particular address on the array with information about the sample at that position, such as hybridization or binding data, including signal intensity. In some exemplary computer readable formats, the individual samples or molecules in the array are arranged regularly (for example, in a Cartesian grid pattern), which can be correlated to address information by a computer.

An address within the array may be of any suitable shape and size. In some embodiments, the nucleic acids are suspended in a liquid medium and contained within square or rectangular wells on the array substrate. However, the nucleic acids may be contained in regions that are essentially triangular, oval, circular, or irregular. The overall shape of the array itself also may vary, though in some embodiments it is substantially flat and rectangular or square in shape.

rRNA profiling arrays may vary in structure, composition, and intended functionality, and may be based on either a macroarray or a microarray format, or a combination thereof. Such arrays can include, for example, at least 10, at least 25, at least 50, at least 100, or more addresses, usually with a single type of nucleic acid at each address. In the case of macroarrays, sophisticated equipment is usually not required to detect a hybridization signal on the array, though quantification may be assisted by standard scanning and/or quantification techniques and equipment. Thus, macroarray analysis as described herein can be carried out in most hospitals, agricultural and medial research laboratories, universities, or other institutions without the need for investment in specialized and expensive reading equipment.

Examples of substrates for the phage arrays disclosed herein include glass (e.g., functionalized glass), Si, Ge, GaAs, GaP, $SiO_2$, $SiN_4$, modified silicon nitrocellulose, polyvinylidene fluoride, polystyrene, polytetrafluoroethylene, polycarbonate, nylon, fiber, or combinations thereof. Array substrates can be stiff and relatively inflexible (for example glass or a supported membrane) or flexible (such as a polymer membrane). One commercially available product line suitable for probe arrays described herein is the Microlite line of MICROTITER® plates available from Dynex Technologies UK (Middlesex, United Kingdom), such as the Microlite 1+96-well plate, or the 384 Microlite+384-well plate.

Addresses on the array should be discrete, in that hybridization signals from individual addresses can be distinguished from signals of neighboring addresses, either by the naked eye (macroarrays) or by scanning or reading by a piece of equipment or with the assistance of a microscope (microarrays).

The following examples are provided to illustrate certain particular features and/or embodiments. These examples should not be construed to limit the invention to the particular features or embodiments described.

EXAMPLES

Example 1

Sequence Search

Sequence data from closely related organisms was analyzed and aligned to see if there were any stretches of 100 nucleotides with sufficient sequence divergence to allow for selective hybridization. For even the most-related organisms, *Escherichia coli* and *Klebsiella pneumoniae*, there were such regions.

Sequences were gathered from every ribosomal RNA gene (up to approximately 5-6 per genome for each subunit) from all sequenced genomes in the NCBI database for the four organisms in the pilot (*Escherichia coli, Klebsiella pneumoniae, Pseudomonas aeruginosa*, and *Staphylococcus aureus*). Of the 23S rRNA sequences, 133 sequences were derived from *Escherichia coli*, 23 from *Klebsiella pneumoniae*, nine from *Pseudomonas aeruginosa*, and 54 from *Staphylococcus aureus*; of the 16S rRNA sequences, 125 were derived from *Escherichia coli*, 21 from *Klebsiella pneumoniae*, eight from *Pseudomonas aeruginosa*, and 55 from *Staphylococcus aureus*; of the 5S rRNA sequences, 68 were derived from *Escherichia coli*, eight from *Klebsiella pneumoniae*, four from *Pseudomonas aeruginosa*, and 31 from *Staphylococcus aureus*.

A list of approximately 520 possible probes was compiled, which was further pared down to 23 non-overlapping probe sequences. Based on the alignments, and due to the similarity between *Escherichia coli* and *Klebsiella pneumoniae* (both species being enteric Gram-negative rods), of the 23 non-overlapping probe sequences, only 3 were from *Escherichia coli* and only one was from *Klebsiella pneumoniae*. Probes that were shared between *Escherichia coli* and *Klebsiella pneumoniae* but distinct from the other species in question we also sought. This resulted in an additional 10 probes that were shared between these two species. Of the resulting 33 possible probes, 23 were chosen that best represented the 4 species and, of these 23 probes that were tested, 19 worked well enough against the 16 clinical isolates tested to include in the final analysis.

Some species share too much homology between their rRNA subunits for this approach to successfully discriminate between them. While this threshold will vary based on the detection technique (such as those based on RT-PCR, like Fluidigm, versus those based on hybridization, like Nanostring), there will eventually be a line beyond which it will be difficult to separate. However, the conceptual approach still allows one to group organisms into classes of similar rRNA sequence. And because organisms with similar rRNA sequences are more closely related (eg, *Escherichia coli* and *Klebsiella pneumoniae* are both enteric Gram-negative rods, whereas *Pseudomonas aeruginosa* is a non-enteric Gram-negative rod and *Staphylococcus aureus* is a Gram-positive coccus), these organisms that group together and may overlap, will behave in a clinically similar manner and typically respond to similar treatments. Thus it may still be of clinical value to identify something early as "*E. coli*-like" or "*Staph aureus*-like", even if unable to identify the exact species.

Example 2

Trials Using the Pilot Probeset

Capture and reporter probes were designed that selectively anneal to the 5S, 16S, and 23S rRNA of *Escherichia coli, Klebsiella pneumoniae, Pseudomonas aeruginosa*, and *Staphylococcus aureus*, four major clinical pathogens. The pathogens were chosen for the pilot study because they cover a broad range of phylogenetic space among pathogenic microbes: two closely related enteric Gram negative bacilli (*E. coli* and *K. pneumoniae*) and a non-enteric Gram negative *bacillus* (*P. aeruginosa*) of the proteobacteria family, and a Gram positive coccus (*S. aureus*) of the firmicute family. Data from a total of 19 probes that recognize these species was generated and analyzed. The close phylogenetic relationship between the two enteric Gram negative bacilli required that 5 of these probes recognize both *E. coli* and *K. pneumoniae*, although we were also able to generate 3 probes specific to *E. coli* alone, and 1 probe unique to *K. pneumoniae*.

Referring to FIG. 1, trials were carried out pursuant to the manufacturer's protocol, using crude lysates from axenic culture of the organisms listed at the top of each column. X-axes represent individual probes, whose complementarity is identified by colored shading overlaid on the graph. From left to right, the first 3 probes are unique to *E. coli*, the next 5 probes are complementary to both *E. coli* and *K. pneumoniae*, the next 1 probe is unique to *K. pneumoniae*, the next 5 probes are unique to *P. pneumoniae*, and the last 6 probes are unique to *S. aureus*. Y-axes represent normalized fluorescence intensity in NanoString's nCounter™ device. Each graph represents a separate experiment with a separate clinical isolate (4 of each of the species listed at the top of the column); since bacterial loads differed across experiments, each y-axis is separately auto-scaled. Strain names are listed at the top of each graph; RB001, RB002, RB022, and RB023 are clinical isolates of *E coli*, RB039-RB043 are *K. pneumoniae*, RB017-RB020 are *P. aeruginosa*, and RB003, RB004, RB006, and RB0007 are *S. aureus*.

Validation proceeded with this probeset on 16 clinical isolates of these 4 species, and the correct species was identified by selective hybridization in all 16 cases. This finding supports the notion that the tight evolutionary conservation of ribosomal RNA genes permits widespread recognition among species, despite the wide variation these distinct clinical isolates might exhibit elsewhere in their genome. (These clinical isolates were speciated using conventional biochemical testing, not rRNA gene sequencing, so this result was not merely tautologic).

Example 3

Dilution Series of Clinical Isolates Demonstrates Sensitivity of rRNA Recognition by Nanostring Detection Referring now to FIG. 2, trials were carried out and results plotted as in FIG. 1, per NanoString protocol. *P. aeruginosa* trials (left column) were performed from axenic culture, while *E. coli* trials (right column) were performed from spiked blood samples purified on a spiral microchannel device. Cell count was confirmed by colony forming units.

To illustrate the power of targeting the highly abundant ribosomal RNA transcripts, samples were progressively diluted containing the bacteria of interest to test the limits of detection of this assay (FIG. 2). It was possible to detect as few as 30 *Pseudomonas* bacilli from axenic culture (left panels) with excellent specificity. In separate experiments using spiked blood samples from which the bacteria were separated using a spiral microfluidic device, the limits of detection was pushed even further, specifically recognizing a mere 6 *E. coli* bacilli (right panels). Thus, by targeting rRNA (as opposed to rDNA, or mRNA) by hybridization, it is possible to detect bacilli on a clinically-relevant scale of abundance, without the need for enzymatic signal amplification such as PCR.

While the pilot study involved fewer than two dozen probes, the NanoString format is capable of accommodating hundreds of separate probes in a single hybridization experiment, conceptually allowing for recognition of many different bacteria assuming sufficient sequence space can be found to distinguish them. Other RNA recognition technologies should provide similar results, depending on their tolerance for mismatches/mutations from consensus.

Additional layers of complexity can be enfolded into this design to include probes that will recognize progressively larger groups of related bacteria by targeting more conserved regions of the rRNA subunits. The 5 probes that recognize both *E. coli* and *K. pneumoniae* exemplify this principle; careful probe design should be able to expand these and related probes to encompass all enteric Gram negative bacilli. At one extreme, targeting the most conserved regions of the 16S rRNA should allow for probes that can detect "all" bacteria by rRNA hybridization, similar to so-called "pan-bacterial" PCR primers that also target the 16S rRNA gene. With appropriate probe design, this strategy can be adapted to allow for the recognition of groups of bacteria at various levels in the phylogenetic tree, each of which can inform clinical decision-making such as prognosis and empiric antibiotic selection.

While clinical applications of this strategy are readily apparent, the bacterial identification permitted by this technique can be conceptually applied to environmental, industrial, military/bioterrorist, or forensic samples, essentially any setting where rapid, sensitive, and specific organism identification is crucial. Eukaryotes too have ribosomal RNA that, like its prokaryotic analogues, is tightly conserved and highly abundant. Thus, extension of this strategy to recognition and identification of eukaryotic tissue is simply a matter of designing appropriate complementary probes.

FIG. 3 shows a visualization of data from a large rRNA probeset. This heatmap displays data from the subset of the probes that predominantly recognize only one species. Other probes that recognize multiple species add additional information (eg, genus-level or higher). The display is such that the vertical axis describes the species from which a probe was derived, and the horizontal axis is the species being tested; both axes are ordered the same (alphabetical). Each row (probe-level data) is internally normalized on a gray-scale for the heatmap (i.e., black represents the most-reactive sample against that specific probe). Thus, if the probes had no relationship to the species, there would be a random assortment of blackness on the plot; if the probes specifically recognize their cognate species, the black shading would form a diagonal as we indeed see in FIG. 3, where each probe best recognizes its cognate species (and each species can be readily identified by its probe-recognition pattern).

The advantage of this probeset is that these 11 species (plus *Candida albicans*) comprise >80% of all microorganisms that infect human blood or urine.

Example 4

Sequences

| Organism | SEQ ID NO: | Probe | Forward Probe |
|---|---|---|---|
| A. baumannii | 1 | A.baumannii_16S | GTACCGACCATTGTAGCACGTGTGTAGCCCTGGCCGTAAGGGCCATGATG |
| A. baumannii | 2 | A.baumannii_23S | TCCAACCTATCAACGTCCTAGTCTCGAACGGCTCTTTAGAGGACATAAAG |
| C. albicans | 3 | C.albicans_18S | ACCGGCCAGCCAAGCCCAAGGTTCAACTACGAGCTTTTTAACTGCAACAA |
| C. albicans | 4 | C.albicans_25S | CCCTAAGACCCCATCTCCGGATAAACCAATTCCAGGGTGATAAGCTGTTA |
| E. cloacae | 5 | E.cloacae_23S | TGCGACTTTCCAGACGCTTCCACTAACACACAAGCTGATTCAGACTCTGG |
| E. coli | 6 | E.coli_16S | ACCAGGTAAGGTTCTTCGCGTTGCATCGAATTAAACCACATGCTCCACCG |
| E. coli | 7 | E.coli_23S | TCACTGAGTCTCGGGTGGAGACAGCCTGGCCATCATTACGCCATTCGTGC |
| E. faecalis | 8 | E.faecalis_23S | TTAACTCTACTCAAGACTCATTGCTTGGACATGCACTTCCAATCGCATGC |
| E. faecium | 9 | E.faecium_16S | ACCTGTTTCCAAGTGTTATCCCCTTCTGATGGGCAGGTTACCCACGTGTT |
| E. faecium | 10 | E.faecium_23S | TTTCCAAGTCATTCGACTATCTGAAAGAACTACCATATTGGAGTCCTACA |
| E. coli | 11 | EC_16S_1370 | ACTCCCATGGTGTGACGGGCGGTGTGTACAAGGCCCGGGAACGTATTCAC |
| E. coli | 12 | EC_16S_140 | TTGCGACGTTATGCGGTATTAGCTACCGTTTCCAGTAGTTATCCCCCTCC |
| E. coli | 13 | EC_16S_5 | TGTGTTAGGCCTGCCGCCAGCGTTCAATCTGAGCCATGATCAAACTCTTC |
| E. coli | 14 | EC_16S_935 | GGTAAGGTTCTTCGCGTTGCATCGAATTAAACCACATGCTCCACCGCTTG |
| E. coli | 15 | EC_23S_1060 | CGACCAGTGAGCTATTACGCTTTCTTTAAATGATGGCTGCTTCTAAGCCA |
| E. coli | 16 | EC_23S_2265 | CTGATGTCCGACCAGGATTAGCCAACCTTCGTGCTCCTCCGTTACTCTTT |
| E. coli | 17 | EC_23S_254 | ACGCTTCCACTAACACACACACTGATTCAGGCTCTGGGCTGCTCCCCGTT |
| E. coli | 18 | EC_23S_675 | CAGTTAGTGTTACCCAACCTTCAACCTGCCCATGGCTAGATCACCGGGTT |
| K. pneumoniae | 19 | K.pneumoniae_23S | TGCCTTCTCCCGAAGTTACGGCACCATTTTGCCTAGTTCCTTCACCCGAG |
| K. pneumoniae | 20 | KP_16S_1050 | TTGCGGGACTTAACCCAACATTTCACAACACGAGCTGACGACAGCCATGC |
| K. pneumoniae | 21 | KP_16S_510 | TAATTCCGATTAACGCTTGCACCCTCCGTATTACCGCGGCTGCTGGCACG |
| K. pneumoniae | 22 | KP_23S_1210 | ATGTCAGCATTCGCACTTCTGATACCTCCAGCATGCCTCACAGCACACCT |
| K. pneumoniae | 23 | KP_23S_260 | TTCCAGACCGTTCCACTAACACACAAGCTGATTCAGACTCTGGGCTGCTC |
| K. pneumoniae | 24 | KP_23S_2790 | CGGCCTATCAACGTCGTCGTCTTCAACGTTCCTTCAGGAGACTTAAAGTC |
| K. pneumoniae | 25 | KP_23S_5 | CCTTCATCGCCTCTGACTGCCAGGGCATCCACCGTGTACGCTTAGTCGCT |
| P. aeruginosa | 26 | P.aeruginosa_23S | CATCAACCACTTCGTCATCTAAAAGACGACTCGTCATCAGCTCTCGGCCT |
| P. mirabilis | 27 | P.mirabilis_23S | CGGACTTTCCAGACCGTTCTCCTGACACTGCTATTGATTAAGACTCTGGG |
| P. aeruginosa | 28 | PA_16S_1190 | ACCGACCATTGTAGCACGTGTGTAGCCCTGGCCGTAAGGGCCATGATGAC |
| P. aeruginosa | 29 | PA_16S_165 | CATCTGATAGCGTGAGGTCCGAAGATCCCCCACTTTCTCCCTCAGGACGT |
| P. aeruginosa | 30 | PA_23S_1375 | AGCCTTCTCCGTCCCTCCATCGCAGTAACCAGAAGTACAGGAATATTAAC |
| P. aeruginosa | 31 | PA_23S_2605 | CGGTCCTCTCGTACTAGGAGCAGCCCCTCTCAAATCTCAAACGTCCACGG |
| P. aeruginosa | 32 | PA_23S_525 | CGCTGACCCATTATACAAAAGGTACGCAGTCACCTAACAAGTAGGCTCCC |
| P. aeruginosa | 33 | PA_5S_200 | ATAAGAACGGCGGCGCGTGCGGAAAATGGCGGGCCTGAAATGGAGGCGG |
| P. aeruginosa | 34 | PA_5S_320 | TGAAGACGTTCGAGGAAATGAAGCGCAGCGGAGAGATCGAGGAGATACTG |

-continued

| Organism | SEQ ID NO: | | |
|---|---|---|---|
| Pan-Staph | 35 | Pan-Staph | TCAGTGTTACCTGAACTTCAACCTGACCAAGGGTAGATCACCTGGTTTCG |
| Pan-Staph-partial | 36 | Pan-Staph-partial | TCCTGTACAAGCTGTGCCGAATTTCAATATCAGGCTACAGTAAAGCTCCA |
| S.agalactiae | 37 | S.agalactiae_16S | CAACAGAGCTTTACGATCCGAAAACCTTCTTCACTCACGCGGCGTTGCTC |
| S.agalactiae | 38 | S.agalactiae_23S | GTAGTATCCCAACAACGCCTCAAACGAAACTGGCGTCCCGTTATCATAGG |
| S.agalactiae | 39 | S.aureus_23S | TTAGACGTGCAATCCAATCGCACGCTTCGCCTATCCTACTGCGTCCCCCC |
| S. maltophilia | 40 | S.maltophilia_16S | CCCTGGCCGTAAGGGCCATGATGACTTGACGTCATCCCCACCTTCCTCCG |
| S. maltophilia | 41 | S.maltophilia_23S | TACTTACACACCTGACCTATCAACCACGTAGTCTACATGGTTCCTTCAGG |
| S aureus | 42 | SA_16S_130 | ATCCGGTATTAGCTCCGGTTTCCCGAAGTTATCCCAGTCTTATAGGTAGG |
| S aureus | 43 | SA_16S_1405 | ACTCCACCGGCTTCGGGTGTTACAAACTCTCGTGGTGTGACGGGCGGTGT |
| S aureus | 44 | SA_16S_355 | GTTGCTCCGTCAGGCTTTCGCCCATTGCGGAAGATTCCCTACTGCTGCCT |
| S aureus | 45 | SA_16S_585 | CCACGGTTGAGCCGTGGGCTTTCACATCAGACTTAAAAAACCGCCTACGC |
| S aureus | 46 | SA_23S_0 | ATCGGCTTCTAGTGCCAAGGCATCCACCGTGCGCCCTTAATAACTTAATC |
| S aureus | 47 | SA_23S_1010 | ATATATTTTGGGACCTTAGCTGGTGGTCTGGGCTGTTTCCCTTTCGAACA |
| S aureus | 48 | SA_23S_1350 | GGCCTCAGCTTAGGACCCGACTAACCCAGAGCGGACGAGCCTTCCTCTGG |
| S aureus | 49 | SA_23S_175 | TTCTCTTCCTCCGGGTACTAAGATGTTTCAGTTCTCCGGGTGTGCCTTCT |
| S aureus | 50 | SA_23S_1960 | AATCGTTACGCCTTTCGTGCGGGTCGGAACTTACCCGACAAGGAATTTCG |
| S aureus | 51 | SA_23S_2505 | AGCCCCAGGATGCGATGAGCCGACATCGAGGTGCCAAACCTCCCCGTCGA |
| S aureus | 52 | SA_23S_655 | AATACTAAACGCCCTATTCAGACTCGCTTTCGCTACGGCTCCACATTTAC |
| S aureus | 53 | SA_5S_15 | CTAAGGAGCTTAACTTCTGTGTTCGGCATGGGAACAGGTGTGACCTCCTT |

| Organism | SEQ ID NO: | | Reverse Probe |
|---|---|---|---|
| A. baumannii | 54 | A.baumannii_16S | TACGATCGGCTTTTTGAGATTAGCATCACATCGCTGTGTAGCAACCCTTT |
| A. baumannii | 55 | A.baumannii_23S | CTCACGCAGCAATTAGTATTGGTCAGCTTCACATATCACTATGCTTCCACA |
| C. albicans | 56 | C.albicans_18S | CTACCCAGAAGGAAAGGCTCGGCTGGGTCCAGTACGCATCAAAAAGATGG |
| C. albicans | 57 | C.albicans_25S | AGGACCGTCGTAAGCGCACCGGACGCGGCAAAATTACCGCGCTCTTCCAG |
| E. cloacae | 58 | E.cloacae_23S | CGAGTTCACAGCCTGTGTGTTTTCGTGTACGGGACTTTCACCCTGTACCG |
| E. coli | 59 | E.coli_16S | CAGTTCCCGAAGGCACCCTCGTATCTCTACAAGGTTCTGTGGATGTCAAG |
| E. coli | 60 | E.coli_23S | TCCGTCTTGCCGCGGGTTACACTTGCATTCTTTTCACAGCGAGTTCAATT |
| E. faecalis | 61 | E.faecalis_23S | CTACTATTATTTCGCTCCCCGTCACAACTTGTCCTTAGAGAGTAAAGCAT |
| E. faecium | 62 | E.faecium_16S | GCGCCTTTCAAATCAAAACCATGCGGTTTCGATTGTTATACGGTATTAGC |
| E. faecium | 63 | E.faecium_23S | AGGTGTCTTCCACATTTCGTCTACGGGGTTTTTACCCTCTTTGACTGACT |
| E. coli | 64 | EC_16S_1370 | AGTGGTAAGCGCCCTCCCGAAGGTTAAGCTACCTACTTCTTTTGCAACCC |
| E. coli | 65 | EC_16S_140 | CATCTGGGCACATCCGATGGCAAGAGGCCCGAGGGTCCCCCTCTTTGGTC |
| E. coli | 66 | EC_16S_5 | CCACTCGTCAGCGAAACAGCAAGCTGCTTCCTGTTACCGTTCGACTTGCA |
| E. coli | 67 | EC_16S_935 | TCCCGAAGGCACATTCTCATCTCTGAAAACTTCCGTGGATGTCAAGACCA |
| E. coli | 68 | EC_23S_1060 | CAGCTTCGGTGCATGGTTTAGCCCCGTTACATCTTCCGCGCAGGCCGACT |
| E. coli | 69 | EC_23S_2265 | CGCGCCGTCACGCTCGCAGTCAAGCTGGCTTATGCCATTGCACTAACCTC |
| E. coli | 70 | EC_23S_254 | TGTGCATTTTTGTGTACGGGGCTGTCACCCTGTATCGCACGCCTTTCCAG |
| E. coli | 71 | EC_23S_675 | CCAGCCACAAGTCATCCGCTAATTTTTCAACATTAGTCGGTTCGGTCCTC |
| K. pneumoniae | 72 | K.pneumoniae_23S | CTTCGACTGGTCTCAGCTCCATCCGCAGGGACTTCACCTACACACCAGCG |

-continued

| Organism | SEQ ID NO: | | Target Sequence |
|---|---|---|---|
| K. pneumoniae | 73 | KP_16S_1050 | TTTGAGTTCCCGGCCGAACCGCTGGCAACAAAGGATAAGGGTTGCGCTCG |
| K. pneumoniae | 74 | KP_16S_510 | GGGATTTCACATCCGACTTGACAGACCGCCTGCGTGCGCTTTACGCCCAG |
| K. pneumoniae | 75 | KP_23S_1210 | AACCCTTGGTCTTCCGGCGAGCGGGCTTTTCACCCGCTTTATCGTTACTT |
| K. pneumoniae | 76 | KP_23S_260 | ACAGCCTGTGCATTTTGGTGTACGGGACTATCACCCTGTACCGTCGGACT |
| K. pneumoniae | 77 | KP_23S_2790 | CACGGTTCATTAGTACCGGTTAGCTCAACGCATCGCTGCGCTTACACACC |
| K. pneumoniae | 78 | KP_23S_5 | GCTGTAACGGTTCATATCACCTTACCGACGCTTTTCGCAGATTAGCACGT |
| P. aeruginosa | 79 | P.aeruginosa_23S | GGTACGGTTCCTGGTTACCTGAAGCTTAGAAGCTTTTCTTGGAAGCATGG |
| P. mirabilis | 80 | P.mirabilis_23S | GAGTTCACAATAACAGCATCTTCAGATACGGGGCTATCACCCTTTACTGC |
| P. aeruginosa | 81 | PA_16S_1190 | CGATCGGTTTTATGGGATTAGCTCCACCTCGCGGCTTGGCAACCCTTTGT |
| P. aeruginosa | 82 | PA_16S_165 | GTCGCCTTGGTAGGCCTTTACCCCACCAACTAGCTAATCCGACCTAGGCT |
| P. aeruginosa | 83 | PA_23S_1375 | AGATTTCAGCCTACCACCTTAAACTTGGACAACCAACGCCAAGCTGGCCT |
| P. aeruginosa | 84 | PA_23S_2605 | CCGGCAATGCCACTGGCGTGACAACCGGAACACCAGAGGTTCGTCCACTC |
| P. aeruginosa | 85 | PA_23S_525 | GCTTTCGCTACGCCTACCCTATACGGTTAAGCTTGCCACTGAATATAAGT |
| P. aeruginosa | 86 | PA_5S_200 | GAGGAAATGAAGCGCAGCGGAGAGATCGAGGAGATACTGCAGCGCTACCG |
| P. aeruginosa | 87 | PA_5S_320 | GGTGAGCTGCATGGTGCGGGACTCCGCAGAGGTTCCGGTGGAAGCGATAC |
| Pan-Staph | 88 | Pan-Staph | CCCTCAGTTCATCCGCTCACTTTTCAACGTAAGTCGGTTCGGTCCTCCAT |
| Pan-Staph-partial | 89 | Pan-Staph-partial | ACCAGCGCCTCCACGTAAGCTAGCGCTCACGTTTCAAAGGCTCCTACCTA |
| S.agalactiae | 90 | S.agalactiae_16S | AGTTACCGTCACTTGGTAGATTTTCCACTCCTACCAACGTTCTTCTCTAA |
| S.agalactiae | 91 | S.agalactiae_23S | TGTCTCCGATAGGGATTGCCTATCTGGGTTAGAGTAGCCATAACACAAGG |
| S.agalactiae | 92 | S.aureus_23S | CAGCTCAGCCTTAATGAGTACCGGATTTGCCTAATACTCAGCCTTACTGC |
| S. maltophilia | 93 | S.maltophilia_16S | CCGTCGCCGGCTTGCAGCCCTCTGTCCCTACCATTGTAGTACGTGTGTAG |
| S. maltophilia | 94 | S.maltophilia_23S | ATGGTCAAGCCGCACGGATCATTAGTATCAGTTAGCTCAATACATTGCTG |
| S aureus | 95 | SA_16S_130 | AGTGACAGCAAGACCGTCTTTCACTTTCGAACCATGCGGTTCAAAATATT |
| S aureus | 96 | SA_16S_1405 | CTTCACCCCAATCATTTGTCCCACCTTCGACGGCTAGTTCCTAAAAGGTT |
| S aureus | 97 | SA_16S_355 | TCCCTAATAACAGAGTTTTACGATCCGAAGACCTTCATCACTCACGCGGC |
| S aureus | 98 | SA_16S_585 | AATTCCACTTTCCTCTTCTGCACTCAAGTTTTCCAGTTTCCAATGACCCT |
| S aureus | 99 | SA_23S_0 | AAAGCTTACTTACAGCTCCCCAAAGCATATCGTCGTTAGTAACGTCCTTC |
| S aureus | 100 | SA_23S_1010 | AAGCCAACATCCTAGTTGTCTGGGCAACGCCACATCCTTTTCCACTTAAC |
| S aureus | 101 | SA_23S_1350 | TTATAGGTGGTACAGGAATATCAACCTGTTATCCATCGCCTACGCCTGTC |
| S aureus | 102 | SA_23S_175 | TTTGGGCTCTTCCCGTTTCGCTCGCCGCTACTAAGGGAATCGAATTTTCT |
| S aureus | 103 | SA_23S_1960 | TCTTCACAGGTACTATGATTTCACCGAGTCTCTCGTTGAGACAGTGCCCA |
| S aureus | 104 | SA_23S_2505 | CTCGCGTACCGCTTTAATGGGCGAACAGCCCAACCCTTGGGACCGACTAC |
| S aureus | 105 | SA_23S_655 | GAACTTCAACCTGACCAAGGGTAGATCACCTGGTTTCGGGTCTACGACCA |
| S aureus | 106 | SA_5S_15 | GCCTGGCAACGTTCTACTCTAGCGGAACGTAAGTTCGACTACCATCGACG |
| Organism | SEQ ID NO: | | Target Sequence |
| A. baumannii | 107 | | CATCATGGCCCTTACGGCCAGGGCTACACACGTGCTACAATGGTCGGTACAAAGGGTTGCTACAC<br>AGCGATGTGATGCTAATCTCAAAAAGCCGATCGTA |
| A. baumannii | 108 | | CTTTATGTCCTCTAAAGAGCCGTTCGAGACTAGGACGTTGATAGGTTGGATGTGGAAGCATAGTG<br>ATATGTGAAGCTGACCAATACTAATTGCTCGTGAG |
| C. albicans | 109 | | TTGTTGCAGTTAAAAAGCTCGTAGTTGAACCTTGGGCTTGGCTGGCCGGTCCATCTTTTTGATGC<br>GTACTGGACCCAGCCGAGCCTTTCCTTCTGGGTAG |

-continued

| | | |
|---|---|---|
| C. albicans | 110 | TAACAGCTTATCACCCTGGAATTGGTTTATCCGGAGATGGGGTCTTAGGGCTGGAAGAGCGCGGT<br>AATTTTGCCGCGTCCGGTGCGCTTACGACGGTCCT |
| E. cloacae | 111 | CCAGAGTCTGAATCAGCTTGTGTGTTAGTGGAAGCGTCTGGAAAGTCGCACGGTACAGGGTGAAA<br>GTCCCGTACACGAAAACACACAGGCTGTGAACTCG |
| E. coli | 112 | CGGTGGAGCATGTGGTTTAATTCGATGCAACGCGAAGAACCTTACCTGGTCTTGACATCCACAGA<br>ACCTTGTAGAGATACGAGGGTGCCTTCGGGAACTG |
| E. coli | 113 | GCACGAATGGCGTAATGATGGCCAGGCTGTCTCCACCCGAGACTCAGTGAAATTGAACTCGCTGT<br>GAAAAGAATGCAAGTGTAACCCGCGGCAAGACGGA |
| E. faecalis | 114 | GCATGCGATTGGAAGTGCATGTCCAAGCAATGAGTCTTGAGTAGAGTTAAATGCTTTACTCTCTA<br>AGGACAAGTTGTGACGGGGAGCGAAATAATAGTAG |
| E. faecium | 115 | AACACGTGGGTAACCTGCCCATCAGAAGGGGATAACACTTGGAAACAGGTGCTAATACCGTATAA<br>CAATCGAAACCGCATGGTTTTGATTTGAAAGGCGC |
| E. faecium | 116 | TGTAGGACTCCAATATGGTAGTTCTTTCAGATAGTCGAATGACTTGGAAAAGTCAGTCAAAGAGG<br>GTAAAAACCCCGTAGACGAAATGTGGAAGCACCT |
| E. coli | 117 | GTGAATACGTTCCCGGGCCTTGTACACACCGCCCGTCACACCATGGGAGTGGGTTGCAAAAGAAG<br>TAGGTAGCTTAACCTTCGGGAGGGCGCTTACCACT |
| E. coli | 118 | GGAGGGGGATAACTACTGGAAACGGTAGCTAATACCGCATAACGTCGCAAGACCAAAGAGGGGGA<br>CCCTCGGGCCTCTTGCCATCGGATGTGCCCAGATG |
| E. coli | 119 | GAAGAGTTTGATCATGGCTCAGATTGAACGCTGGCGGCAGGCCTAACACATGCAAGTCGAACGGT<br>AACAGGAAGCAGCTTGCTGTTTCGCTGACGAGTGG |
| E. coli | 120 | CAAGCGGTGGAGCATGTGGTTTAATTCGATGCAACGCGAAGAACCTTACCTGGTCTTGACATCCA<br>CGGAAGTTTTCAGAGATGAGAATGTGCCTTCGGGA |
| E. coli | 121 | TGGCTTAGAAGCAGCCATCATTTAAAGAAAGCGTAATAGCTCACTGGTCGAGTCGGCCTGCGCGG<br>AAGATGTAACGGGGCTAAACCATGCACCGAAGCTG |
| E. coli | 122 | AAAGAGTAACGGAGGAGCACGAAGGTTGGCTAATCCTGGTCGGACATCAGGAGGTTAGTGCAATG<br>GCATAAGCCAGCTTGACTGCGAGCGTGACGGCGCG |
| E. coli | 123 | AACGGGGAGCAGCCCAGAGCCTGAATCAGTGTGTGTGTTAGTGGAAGCGTCTGGAAAGGCGTGCG<br>ATACAGGGTGACAGCCCCGTACACAAAAATGCACA |
| E. coli | 124 | AACCCGGTGATCTAGCCATGGGCAGGTTGAAGGTTGGGTAACACTAACTGGAGGACCGAACCGAC<br>TAATGTTGAAAAATTAGCGGATGACTTGTGGCTGG |
| K. pneumoniae | 125 | CTCGGGTGAAGGAACTAGGCAAAATGGTGCCGTAACTTCGGGAGAAGGCACGCTGGTGTGTAGGT<br>GAAGTCCCTGCGGATGGAGCTGAGACCAGTCGAAG |
| K. pneumoniae | 126 | GCATGGCTGTCGTCAGCTCGTGTTGTGAAATGTTGGGTTAAGTCCCGCAACGAGCGCAACCCTTA<br>TCCTTTGTTGCCAGCGGTTCGGCCGGGAACTCAAA |
| K. pneumoniae | 127 | CGTGCCAGCAGCCGCGGTAATACGGAGGGTGCAAGCGTTAATCGGAATTACTGGGCGTAAAGCGC<br>ACGCAGGCGGTCTGTCAAGTCGGATGTGAAATCCC |
| K. pneumoniae | 128 | AGGTGTGCTGTGAGGCATGCTGGAGGTATCAGAAGTGCGAATGCTGACATAAGTAACGATAAAGC<br>GGGTGAAAAGCCCGCTCGCCGGAAGACCAAGGGTT |
| K. pneumoniae | 129 | GAGCAGCCCAGAGTCTGAATCAGCTTGTGTGTTAGTGGAACGGTCTGGAAAGTCCGACGGTACAG<br>GGTGATAGTCCCGTACACCAAAATGCACAGGCTGT |
| K. pneumoniae | 130 | GACTTTAAGTCTCCTGAAGGAACGTTGAAGACGACGACGTTGATAGGCCGGGTGTGTAAGCGCAG<br>CGATGCGTTGAGCTAACCGGTACTAATGAACCGTG |
| K. pneumoniae | 131 | AGCGACTAAGCGTACACGGTGGATGCCCTGGCAGTCAGAGGCGATGAAGGACGTGCTAATCTGCG<br>AAAAGCGTCGGTAAGGTGATATGAACCGTTACAGC |
| P. aeruginosa | 132 | AGGCCGAGAGCTGATGACGAGTCGTCTTTTAGATGACGAAGTGGTTGATGCCATGCTTCCAAGAA<br>AAGCTTCTAAGCTTCAGGTAACCAGGAACCGTACC |
| P. mirabilis | 133 | CCCAGAGTCTTAATCAATAGCAGTGTCAGGAGAACGGTCTGGAAAGTCCGGCAGTAAAGGGTGAT<br>AGCCCCGTATCTGAAGATGCTGTTATTGTGAACTC |
| P. aeruginosa | 134 | GTCATCATGGCCCTTACGGCCAGGGCTACACACGTGCTACAATGGTCGGTACAAAGGGTTGCCAA<br>GCCGCGAGGTGGAGCTAATCCCATAAAACCGATCG |
| P. aeruginosa | 135 | ACGTCCTGAGGGAGAAAGTGGGGGATCTTCGGACCTCACGCTATCAGATGAGCCTAGGTCGGATT<br>AGCTAGTTGGTGGGGTAAAGGCCTACCAAGGCGAC |

-continued

| | | |
|---|---|---|
| P. aeruginosa | 136 | GTTAATATTCCTGTACTTCTGGTTACTGCGATGGAGGGACGGAGAAGGCTAGGCCAGCTTGGCGT TGGTTGTCCAAGTTTAAGGTGGTAGGCTGAAATCT |
| P. aeruginosa | 137 | CCGTGGACGTTTGAGATTTGAGAGGGGCTGCTCCTAGTACGAGAGGACCGGAGTGGACGAACCTC TGGTGTTCCGGTTGTCACGCCAGTGGCATTGCCGG |
| P. aeruginosa | 138 | GGGAGCCTACTTGTTAGGTGACTGCGTACCTTTTGTATAATGGGTCAGCGACTTATATTCAGTGG CAAGCTTAACCGTATAGGGTAGGCGTAGCGAAAGC |
| P. aeruginosa | 139 | CCGCCTCCATTTCAGGCCCGCCATTTTCCGCACGCCGCCGCCGTTCTTATCGGTAGCGCTGCAGT ATCTCCTCGATCTCTCCGCTGCGCTTCATTTCCTC |
| P. aeruginosa | 140 | CAGTATCTCCTCGATCTCTCCGCTGCGCTTCATTTCCTCGAACGTCTTCAGTATCGCTTCCACCG GAACCTCTGCGGAGTCCCGCACCATGCAGCTCACC |
| Pan-Staph | 141 | CGAAACCAGGTGATCTACCCTTGGTCAGGTTGAAGTTCAGGTAACACTGAATGGAGGACCGAACC GACTTACGTTGAAAAGTGAGCGGATGAACTGAGGG |
| Pan-Staph-partial | 142 | TGGAGCTTTACTGTAGCCTGATATTGAAATTCGGCACAGCTTGTACAGGATAGGTAGGAGCCTTT GAAACGTGAGCGCTAGCTTACGTGGAGGCGCTGGT |
| S.agalactiae | 143 | GAGCAACGCCGCGTGAGTGAAGAAGGTTTTCGGATCGTAAAGCTCTGTTGTTAGAGAAGAACGTT GGTAGGAGTGGAAAATCTACCAAGTGACGGTAACT |
| S.agalactiae | 144 | CCTATGATAACGGGACGCCAGTTTCGTTTGAGGCGTTGTTGGGATACTACCCTTGTGTTATGGCT ACTCTAACCCAGATAGGCAATCCCTATCGGAGACA |
| S.agalactiae | 145 | GGGGGGACGCAGTAGGATAGGCGAAGCGTGCGATTGGATTGCACGTCTAAGCAGTAAGGCTGAGT ATTAGGCAAATCCGGTACTCATTAAGGCTGAGCTG |
| S. maltophilia | 146 | CGGAGGAAGGTGGGGATGACGTCAAGTCATCATGGCCCTTACGGCCAGGGCTACACACGTACTAC AATGGTAGGGACAGAGGGCTGCAAGCCGGCGACGG |
| S. maltophilia | 147 | CCTGAAGGAACCATGTAGACTACGTGGTTGATAGGTCAGGTGTGTAAGTACAGCAATGTATTGAG CTAACTGATACTAATGATCCGTGCGGCTTGACCAT |
| S aureus | 148 | CCTACCTATAAGACTGGGATAACTTCGGGAAACCGGAGCTAATACCGGATAATATTTTGAACCGC ATGGTTCGAAAGTGAAAGACGGTCTTGCTGTCACT |
| S aureus | 149 | ACACCGCCCGTCACACCACGAGAGTTTGTAACACCCGAAGCCGGTGGAGTAACCTTTTAGGAACT AGCCGTCGAAGGTGGGACAAATGATTGGGGTGAAG |
| S aureus | 150 | AGGCAGCAGTAGGGAATCTTCCGCAATGGGCGAAAGCCTGACGGAGCAACGCCGCGTGAGTGATG AAGGTCTTCGGATCGTAAAACTCTGTTATTAGGGA |
| S aureus | 151 | GCGTAGGCGGTTTTTTAAGTCTGATGTGAAAGCCCACGGCTCAACCGTGGAGGGTCATTGGAAAC TGGAAAACTTGAGTGCAGAAGAGGAAAGTGGAATT |
| S aureus | 152 | GATTAAGTTATTAAGGGCGCACGGTGGATGCCTTGGCACTAGAAGCCGATGAAGGACGTTACTAA CGACGATATGCTTTGGGGAGCTGTAAGTAAGCTTT |
| S aureus | 153 | TGTTCGAAAGGGAAACAGCCCAGACCACCAGCTAAGGTCCCAAAATATATGTTAAGTGGAAAAGG ATGTGGCGTTGCCCAGACAACTAGGATGTTGGCTT |
| S aureus | 154 | CCAGAGGAAGGCTCGTCCGCTCTGGGTTAGTCGGGTCCTAAGCTGAGGCCGACAGGCGTAGGCGA TGGATAACAGGTTGATATTCCTGTACCACCTATAA |
| S aureus | 155 | AGAAGGCACACCCGGAGAACTGAAACATCTTAGTACCCGGAGGAAGAGAAAGAAAATTCGATTCC CTTAGTAGCGGCGAGCGAAACGGGAAGAGCCCAAA |
| S aureus | 156 | CGAAATTCCTTGTCGGGTAAGTTCCGACCCGCACGAAAGGCGTAACGATTTGGGCACTGTCTCAA CGAGAGACTCGGTGAAATCATAGTACCTGTGAAGA |
| S aureus | 157 | TCGACGGGGAGGTTTGGCACCTCGATGTCGGCTCATCGCATCCTGGGGCTGTAGTCGGTCCCAAG GGTTGGGCTGTTCGCCCATTAAAGCGGTACGCGAG |
| S aureus | 158 | GTAAATGTGGAGCCGTAGCGAAAGCGAGTCTGAATAGGGCGTTTAGTATTTGGTCGTAGACCCGA AACCAGGTGATCTACCCTTGGTCAGGTTGAAGTTC |
| S aureus | 159 | AAGGAGGTCACACCTGTTCCCATGCCGAACACAGAAGTTAAGCTCCTTAGCGTCGATGGTAGTCG AACTTACGTTCCGCTAGAGTAGAACGTTGCCAGGC |

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

What is claimed is:

1. A method of detecting bacterial rRNA sequences in a sample, comprising:
   contacting a sample with a set of probes, the set of probes comprising a plurality of different probes that hybridize to two or more different 5S target rRNA sequences, wherein each probe shares less than 80% identity with the other probes in the probe set and each probe is between 42 and 160 nucleotides in length,
   hybridizing the set of probes to the target 5S rRNA sequences in the sample, and
   detecting the target 5S rRNA sequences in the sample.

2. The method of claim 1, wherein the probe set comprises one or more probes specific to one or more target rRNA sequences from two or more of *Escherichia coli, Klebsiella pneumoniae, Pseudomonas aeruginosa, Staphylococcus aureus, Acinetobacter baumannii, Candida albicans, Enterobacter cloacae, Enterococcus faecalis, Enterococcus faecium, Proteus mirabilis, Streptococcus agalactiae*, and *Stenotrophomonas maltophilia*.

3. The method of claim 1, wherein the probe set comprises one or more probes specific to one or more target rRNA sequences for each of *Escherichia coli, Klebsiella pneumoniae, Pseudomonas aeruginosa, Staphylococcus aureus, Acinetobacter baumannii, Candida albicans, Enterobacter cloacae, Enterococcus faecalis, Enterococcus faecium, Proteus mirabilis, Streptococcus agalactiae*, and *Stenotrophomonas maltophilia*.

4. The method of claim 1, wherein the probe set comprises one or more probes specific to each of *E. coli, K pneumoniae, P. aeruginosa*, and *S. aureus*.

5. The method of claim 1, wherein the probe set is attached to a solid surface.

6. The method of claim 5, wherein the probe set comprises probe pairs that bind to adjacent regions of a same target rRNA sequence.

7. The method of claim 6, wherein a first probe of each probe pair comprises a detectable label and a second probe of each probe pairs comprises a capture moiety.

8. The method of claim 7, wherein the detectable label is radiolabeled, fluorescently labeled, biotin-labeled, enzymatically-labeled, or chemically-labeled.

9. The method of claim 7, wherein the capture moiety is biotin.

10. The method of claim 7, wherein the first or second probe is bound to a solid surface.

* * * * *

UNITED STATES PATENT AND TRADEMARK OFFICE
CERTIFICATE OF CORRECTION

PATENT NO. : 11,441,196 B2
APPLICATION NO. : 14/775296
DATED : September 13, 2022
INVENTOR(S) : Roby Bhattacharyya et al.

It is certified that error appears in the above-identified patent and that said Letters Patent is hereby corrected as shown below:

In the Specification

In Column 2, Line 25, before "Because" insert -- . --.

In Column 4, Line 60, delete "baumanii," and insert -- baumannii, --.

In Column 4, Line 63, delete "hydrophile," and insert -- hydrophila, --.

In Column 4, Line 66, delete "baumanii," and insert -- baumannii, --.

In Column 5, Line 8, delete "melintensis" and insert -- melitensis --.

In Column 5, Line 17, delete "jeikeum" and insert -- jeikeium --.

In Column 5, Line 27, delete "chafeensia" and insert -- chaffeensis --.

In Column 5, Line 35, delete "kingii," and insert -- kingae, --.

In Column 5, Line 40, delete "hemolytica," and insert -- haemolytica, --.

In Column 5, Line 45, delete "Mycoplasm" and insert -- Mycoplasma --.

In Column 5, Line 62, delete "cholerasuis" and insert -- choleraesuis --.

In Column 5, Line 64, delete "marcesans" and insert -- marcescens --.

In Column 5, Line 64, delete "liquifaciens)," and insert -- liquefaciens), --.

In Column 6, Line 1, delete "hemolyticus," and insert -- haemolyticus, --.

Signed and Sealed this
Twenty-third Day of May, 2023

Katherine Kelly Vidal
*Director of the United States Patent and Trademark Office*

CERTIFICATE OF CORRECTION (continued)
U.S. Pat. No. 11,441,196 B2

In Column 6, Line 25, delete "equismilis," and insert -- equisimilis, --.

In Column 6, Line 28, delete "moniliformi," and insert -- moniliformis, --.

In Column 6, Line 29, delete "petenue," and insert -- pertenue, --.

In Column 6, Line 30, delete "whippelii," and insert -- whippeli, --.

In Column 6, Line 32, delete "parahemolyticus," and insert -- parahaemolyticus, --.

In Column 6, Line 35, delete "metchnikovii," and insert -- metschnikovii, --.

In Column 6, Line 35, delete "furnisii)," and insert -- furnissii), --.

In Column 7, Line 50, delete "trifluoromethylcoumuarin" and insert -- trifluoromethylcoumarin --.

In Column 7, Line 51, delete "diaminidino" and insert -- diamidino --.

In Column 11, Line 35, delete "galactosylqueosine," and insert -- galactosylqueuosine, --.

In Column 11, Line 35, delete "N-6-sopentenyladenine," and insert -- N~6-isopentenyladenine, --.

In Column 11, Line 40, delete "mannosylqueosine," and insert -- mannosylqueuosine, --.

In Column 11, Line 42, delete "queosine," and insert -- queuosine, --.

In Column 11, Line 54, delete "phosphordiamidate," and insert -- phosphorodiamidate, --.

In Column 17, Line 55, delete "baumanniii," and insert -- baumannii, --.

In Column 20, Line 25, delete "baumanniii." and insert -- baumannii. --.

In Column 21, Line 43, delete "probes" and insert -- probes. --.

In Column 26, Line 7, delete "thereof" and insert -- thereof. --.

SEQUENCE LISTING

<160> NUMBER OF SEQ ID NOS: 159

<210> SEQ ID NO 1
<211> LENGTH: 50
<212> TYPE: DNA
<213> ORGANISM: Acinetobacter baumannii

<400> SEQUENCE: 1
gtaccgacca ttgtagcacg tgtgtagccc tggccgtaag ggccatgatg                50

<210> SEQ ID NO 2
<211> LENGTH: 50
<212> TYPE: DNA
<213> ORGANISM: Acinetobacter baumannii

<400> SEQUENCE: 2
tccaacctat caacgtccta gtctcgaacg gctctttaga ggacataaag                50

<210> SEQ ID NO 3
<211> LENGTH: 50
<212> TYPE: DNA
<213> ORGANISM: Candida albicans

<400> SEQUENCE: 3
accggccagc caagcccaag gttcaactac gagcttttta actgcaacaa                50

<210> SEQ ID NO 4
<211> LENGTH: 50
<212> TYPE: DNA
<213> ORGANISM: Candida albicans

<400> SEQUENCE: 4
ccctaagacc ccatctccgg ataaaccaat tccagggtga taagctgtta                50

<210> SEQ ID NO 5
<211> LENGTH: 50
<212> TYPE: DNA
<213> ORGANISM: Enterobacter cloacae

<400> SEQUENCE: 5
tgcgactttc cagacgcttc cactaacaca caagctgatt cagactctgg                50

<210> SEQ ID NO 6
<211> LENGTH: 50
<212> TYPE: DNA
<213> ORGANISM: Escherichia coli

<400> SEQUENCE: 6
accaggtaag gttcttcgcg ttgcatcgaa ttaaaccaca tgctccaccg                50

<210> SEQ ID NO 7
<211> LENGTH: 50
<212> TYPE: DNA
<213> ORGANISM: Escherichia coli

<400> SEQUENCE: 7
tcactgagtc tcgggtggag acagcctggc catcattacg ccattcgtgc                50

<210> SEQ ID NO 8
<211> LENGTH: 50
<212> TYPE: DNA
<213> ORGANISM: Enterococcus faecalis

<400> SEQUENCE: 8
ttaactctac tcaagactca ttgcttggac atgcacttcc aatcgcatgc        50

<210> SEQ ID NO 9
<211> LENGTH: 50
<212> TYPE: DNA
<213> ORGANISM: Enterococcus faecium

<400> SEQUENCE: 9
acctgtttcc aagtgttatc cccttctgat gggcaggtta cccacgtgtt        50

<210> SEQ ID NO 10
<211> LENGTH: 50
<212> TYPE: DNA
<213> ORGANISM: Enterococcus faecium

<400> SEQUENCE: 10
tttccaagtc attcgactat ctgaaagaac taccatattg gagtcctaca        50

<210> SEQ ID NO 11
<211> LENGTH: 50
<212> TYPE: DNA
<213> ORGANISM: Escherichia coli

<400> SEQUENCE: 11
actcccatgg tgtgacgggc ggtgtgtaca aggcccggga acgtattcac        50

<210> SEQ ID NO 12
<211> LENGTH: 50
<212> TYPE: DNA
<213> ORGANISM: Escherichia coli

<400> SEQUENCE: 12
ttgcgacgtt atgcggtatt agctaccgtt tccagtagtt atcccctcc        50

<210> SEQ ID NO 13
<211> LENGTH: 50
<212> TYPE: DNA
<213> ORGANISM: Escherichia coli

<400> SEQUENCE: 13
tgtgttaggc ctgccgccag cgttcaatct gagccatgat caaactcttc        50

<210> SEQ ID NO 14
<211> LENGTH: 50
<212> TYPE: DNA
<213> ORGANISM: Escherichia coli

<400> SEQUENCE: 14
ggtaaggttc ttcgcgttgc atcgaattaa accacatgct ccaccgcttg        50

<210> SEQ ID NO 15
<211> LENGTH: 50
<212> TYPE: DNA
<213> ORGANISM: Escherichia coli

<400> SEQUENCE: 15
cgaccagtga gctattacgc tttctttaaa tgatggctgc ttctaagcca        50

<210> SEQ ID NO 16
<211> LENGTH: 50
<212> TYPE: DNA
<213> ORGANISM: Escherichia coli

<400> SEQUENCE: 16
ctgatgtccg accaggatta gccaaccttc gtgctcctcc gttactcttt                50

<210> SEQ ID NO 17
<211> LENGTH: 50
<212> TYPE: DNA
<213> ORGANISM: Escherichia coli

<400> SEQUENCE: 17
acgcttccac taacacacac actgattcag gctctgggct gctcccgtt                 50

<210> SEQ ID NO 18
<211> LENGTH: 50
<212> TYPE: DNA
<213> ORGANISM: Escherichia coli

<400> SEQUENCE: 18
cagttagtgt tacccaacct tcaacctgcc catggctaga tcaccgggtt               50

<210> SEQ ID NO 19
<211> LENGTH: 50
<212> TYPE: DNA
<213> ORGANISM: Klebsiella pneumoniae

<400> SEQUENCE: 19
tgccttctcc cgaagttacg gcaccatttt gcctagttcc ttcacccgag                50

<210> SEQ ID NO 20
<211> LENGTH: 50
<212> TYPE: DNA
<213> ORGANISM: Klebsiella pneumoniae

<400> SEQUENCE: 20
ttgcgggact taacccaaca tttcacaaca cgagctgacg acagccatgc                50

<210> SEQ ID NO 21
<211> LENGTH: 50
<212> TYPE: DNA
<213> ORGANISM: Klebsiella pneumoniae

<400> SEQUENCE: 21
taattccgat taacgcttgc accctccgta ttaccgcggc tgctggcacg                50

<210> SEQ ID NO 22
<211> LENGTH: 50
<212> TYPE: DNA
<213> ORGANISM: Klebsiella pneumoniae

<400> SEQUENCE: 22
atgtcagcat tcgcacttct gatacctcca gcatgcctca cagcacacct                50

<210> SEQ ID NO 23
<211> LENGTH: 50
<212> TYPE: DNA
<213> ORGANISM: Klebsiella pneumoniae

<400> SEQUENCE: 23
ttccagaccg ttccactaac acacaagctg attcagactc tgggctgctc                50

<210> SEQ ID NO 24
<211> LENGTH: 50
<212> TYPE: DNA
<213> ORGANISM: Klebsiella pneumoniae

```
<400> SEQUENCE: 24
cggcctatca acgtcgtcgt cttcaacgtt ccttcaggag acttaaagtc                50

<210> SEQ ID NO 25
<211> LENGTH: 50
<212> TYPE: DNA
<213> ORGANISM: Klebsiella pneumoniae

<400> SEQUENCE: 25
ccttcatcgc ctctgactgc cagggcatcc accgtgtacg cttagtcgct                50

<210> SEQ ID NO 26
<211> LENGTH: 50
<212> TYPE: DNA
<213> ORGANISM: Pseudomonas aeruginosa

<400> SEQUENCE: 26
catcaaccac ttcgtcatct aaaagacgac tcgtcatcag ctctcggcct                50

<210> SEQ ID NO 27
<211> LENGTH: 50
<212> TYPE: DNA
<213> ORGANISM: Proteus mirabilis

<400> SEQUENCE: 27
cggactttcc agaccgttct cctgacactg ctattgatta agactctggg                50

<210> SEQ ID NO 28
<211> LENGTH: 50
<212> TYPE: DNA
<213> ORGANISM: Pseudomonas aeruginosa

<400> SEQUENCE: 28
accgaccatt gtagcacgtg tgtagccctg gccgtaaggg ccatgatgac                50

<210> SEQ ID NO 29
<211> LENGTH: 50
<212> TYPE: DNA
<213> ORGANISM: Pseudomonas aeruginosa

<400> SEQUENCE: 29
catctgatag cgtgaggtcc gaagatcccc cactttctcc ctcaggacgt                50

<210> SEQ ID NO 30
<211> LENGTH: 50
<212> TYPE: DNA
<213> ORGANISM: Pseudomonas aeruginosa

<400> SEQUENCE: 30
agccttctcc gtccctccat cgcagtaacc agaagtacag gaatattaac               50

<210> SEQ ID NO 31
<211> LENGTH: 50
<212> TYPE: DNA
<213> ORGANISM: Pseudomonas aeruginosa

<400> SEQUENCE: 31
cggtcctctc gtactaggag cagcccctct caaatctcaa acgtccacgg                50

<210> SEQ ID NO 32
<211> LENGTH: 50
<212> TYPE: DNA
```

<213> ORGANISM: Pseudomonas aeruginosa

<400> SEQUENCE: 32
cgctgaccca ttatacaaaa ggtacgcagt cacctaacaa gtaggctccc    50

<210> SEQ ID NO 33
<211> LENGTH: 50
<212> TYPE: DNA
<213> ORGANISM: Pseudomonas aeruginosa

<400> SEQUENCE: 33
ataagaacgg cggcggcgtg cggaaaatgg cgggcctgaa atggaggcgg    50

<210> SEQ ID NO 34
<211> LENGTH: 50
<212> TYPE: DNA
<213> ORGANISM: Pseudomonas aeruginosa

<400> SEQUENCE: 34
tgaagacgtt cgaggaaatg aagcgcagcg gagagatcga ggagatactg    50

<210> SEQ ID NO 35
<211> LENGTH: 50
<212> TYPE: DNA
<213> ORGANISM: Staphylococcus sp.

<400> SEQUENCE: 35
tcagtgttac ctgaacttca acctgaccaa gggtagatca cctggtttcg    50

<210> SEQ ID NO 36
<211> LENGTH: 50
<212> TYPE: DNA
<213> ORGANISM: Staphylococcus sp.

<400> SEQUENCE: 36
tcctgtacaa gctgtgccga atttcaatat caggctacag taaagctcca    50

<210> SEQ ID NO 37
<211> LENGTH: 50
<212> TYPE: DNA
<213> ORGANISM: Streptococcus agalactiae

<400> SEQUENCE: 37
caacagagct ttacgatccg aaaaccttct tcactcacgc ggcgttgctc    50

<210> SEQ ID NO 38
<211> LENGTH: 50
<212> TYPE: DNA
<213> ORGANISM: Streptococcus agalactiae

<400> SEQUENCE: 38
gtagtatccc aacaacgcct caaacgaaac tggcgtcccg ttatcatagg    50

<210> SEQ ID NO 39
<211> LENGTH: 50
<212> TYPE: DNA
<213> ORGANISM: Streptococcus agalactiae

<400> SEQUENCE: 39
ttagacgtgc aatccaatcg cacgcttcgc ctatcctact gcgtccccc    50

<210> SEQ ID NO 40
<211> LENGTH: 50

```
<212> TYPE: DNA
<213> ORGANISM: Stenotrophomonas maltophilia

<400> SEQUENCE: 40
ccctggccgt aagggccatg atgacttgac gtcatcccca ccttcctccg        50

<210> SEQ ID NO 41
<211> LENGTH: 50
<212> TYPE: DNA
<213> ORGANISM: Stenotrophomonas maltophilia

<400> SEQUENCE: 41
tacttacaca cctgacctat caaccacgta gtctacatgg ttccttcagg        50

<210> SEQ ID NO 42
<211> LENGTH: 50
<212> TYPE: DNA
<213> ORGANISM: Staphylococcus aureus

<400> SEQUENCE: 42
atccggtatt agctccggtt tcccgaagtt atcccagtct tataggtagg        50

<210> SEQ ID NO 43
<211> LENGTH: 50
<212> TYPE: DNA
<213> ORGANISM: Staphylococcus aureus

<400> SEQUENCE: 43
actccaccgg cttcgggtgt tacaaactct cgtggtgtga cgggcggtgt        50

<210> SEQ ID NO 44
<211> LENGTH: 50
<212> TYPE: DNA
<213> ORGANISM: Staphylococcus aureus

<400> SEQUENCE: 44
gttgctccgt caggctttcg cccattgcgg aagattccct actgctgcct        50

<210> SEQ ID NO 45
<211> LENGTH: 50
<212> TYPE: DNA
<213> ORGANISM: Staphylococcus aureus

<400> SEQUENCE: 45
ccacggttga gccgtgggct ttcacatcag acttaaaaaa ccgcctacgc        50

<210> SEQ ID NO 46
<211> LENGTH: 50
<212> TYPE: DNA
<213> ORGANISM: Staphylococcus aureus

<400> SEQUENCE: 46
atcggcttct agtgccaagg catccaccgt gcgcccttaa taacttaatc        50

<210> SEQ ID NO 47
<211> LENGTH: 50
<212> TYPE: DNA
<213> ORGANISM: Staphylococcus aureus

<400> SEQUENCE: 47
atatattttg ggaccttagc tggtggtctg ggctgtttcc ctttcgaaca        50

<210> SEQ ID NO 48
```

<211> LENGTH: 50
<212> TYPE: DNA
<213> ORGANISM: Staphylococcus aureus

<400> SEQUENCE: 48
ggcctcagct taggacccga ctaacccaga gcggacgagc cttcctctgg         50

<210> SEQ ID NO 49
<211> LENGTH: 50
<212> TYPE: DNA
<213> ORGANISM: Staphylococcus aureus

<400> SEQUENCE: 49
ttctcttcct ccgggtacta agatgtttca gttctccggg tgtgccttct         50

<210> SEQ ID NO 50
<211> LENGTH: 50
<212> TYPE: DNA
<213> ORGANISM: Staphylococcus aureus

<400> SEQUENCE: 50
aatcgttacg cctttcgtgc gggtcggaac ttacccgaca aggaatttcg         50

<210> SEQ ID NO 51
<211> LENGTH: 50
<212> TYPE: DNA
<213> ORGANISM: Staphylococcus aureus

<400> SEQUENCE: 51
agccccagga tgcgatgagc cgacatcgag gtgccaaacc tccccgtcga         50

<210> SEQ ID NO 52
<211> LENGTH: 50
<212> TYPE: DNA
<213> ORGANISM: Staphylococcus aureus

<400> SEQUENCE: 52
aatactaaac gccctattca gactcgcttt cgctacggct ccacatttac         50

<210> SEQ ID NO 53
<211> LENGTH: 50
<212> TYPE: DNA
<213> ORGANISM: Staphylococcus aureus

<400> SEQUENCE: 53
ctaaggagct taacttctgt gttcggcatg ggaacaggtg tgacctcctt         50

<210> SEQ ID NO 54
<211> LENGTH: 50
<212> TYPE: DNA
<213> ORGANISM: Acinetobacter baumannii

<400> SEQUENCE: 54
tacgatcggc ttttgagat tagcatcaca tcgctgtgta gcaacccttt         50

<210> SEQ ID NO 55
<211> LENGTH: 50
<212> TYPE: DNA
<213> ORGANISM: Acinetobacter baumannii

<400> SEQUENCE: 55
ctcacgagca attagtattg gtcagcttca catatcacta tgcttccaca         50

```
<210> SEQ ID NO 56
<211> LENGTH: 50
<212> TYPE: DNA
<213> ORGANISM: Candida albicans

<400> SEQUENCE: 56
ctacccagaa ggaaaggctc ggctgggtcc agtacgcatc aaaaagatgg            50

<210> SEQ ID NO 57
<211> LENGTH: 50
<212> TYPE: DNA
<213> ORGANISM: Candida albicans

<400> SEQUENCE: 57
aggaccgtcg taagcgcacc ggacgcggca aaattaccgc gctcttccag            50

<210> SEQ ID NO 58
<211> LENGTH: 50
<212> TYPE: DNA
<213> ORGANISM: Enterobacter cloacae

<400> SEQUENCE: 58
cgagttcaca gcctgtgtgt tttcgtgtac gggactttca ccctgtaccg            50

<210> SEQ ID NO 59
<211> LENGTH: 50
<212> TYPE: DNA
<213> ORGANISM: Escherichia coli

<400> SEQUENCE: 59
cagttcccga aggcaccctc gtatctctac aaggttctgt ggatgtcaag            50

<210> SEQ ID NO 60
<211> LENGTH: 50
<212> TYPE: DNA
<213> ORGANISM: Escherichia coli

<400> SEQUENCE: 60
tccgtcttgc cgcgggttac acttgcattc ttttcacagc gagttcaatt            50

<210> SEQ ID NO 61
<211> LENGTH: 50
<212> TYPE: DNA
<213> ORGANISM: Enterococcus faecalis

<400> SEQUENCE: 61
ctactattat ttcgctcccc gtcacaactt gtccttagag agtaaagcat            50

<210> SEQ ID NO 62
<211> LENGTH: 50
<212> TYPE: DNA
<213> ORGANISM: Enterococcus faecium

<400> SEQUENCE: 62
gcgcctttca aatcaaaacc atgcggtttc gattgttata cggtattagc            50

<210> SEQ ID NO 63
<211> LENGTH: 50
<212> TYPE: DNA
<213> ORGANISM: Enterococcus faecium

<400> SEQUENCE: 63
aggtgtcttc cacatttcgt ctacgggggtt tttaccctct ttgactgact           50
```

<210> SEQ ID NO 64
<211> LENGTH: 50
<212> TYPE: DNA
<213> ORGANISM: Escherichia coli

<400> SEQUENCE: 64
agtggtaagc gccctcccga aggttaagct acctacttct tttgcaaccc    50

<210> SEQ ID NO 65
<211> LENGTH: 50
<212> TYPE: DNA
<213> ORGANISM: Escherichia coli

<400> SEQUENCE: 65
catctgggca catccgatgg caagaggccc gagggtcccc ctctttggtc    50

<210> SEQ ID NO 66
<211> LENGTH: 50
<212> TYPE: DNA
<213> ORGANISM: Escherichia coli

<400> SEQUENCE: 66
ccactcgtca gcgaaacagc aagctgcttc ctgttaccgt tcgacttgca    50

<210> SEQ ID NO 67
<211> LENGTH: 50
<212> TYPE: DNA
<213> ORGANISM: Escherichia coli

<400> SEQUENCE: 67
tcccgaaggc acattctcat ctctgaaaac ttccgtggat gtcaagacca    50

<210> SEQ ID NO 68
<211> LENGTH: 50
<212> TYPE: DNA
<213> ORGANISM: Escherichia coli

<400> SEQUENCE: 68
cagcttcggt gcatggttta gccccgttac atcttccgcg caggccgact    50

<210> SEQ ID NO 69
<211> LENGTH: 50
<212> TYPE: DNA
<213> ORGANISM: Escherichia coli

<400> SEQUENCE: 69
cgcgccgtca cgctcgcagt caagctggct tatgccattg cactaacctc    50

<210> SEQ ID NO 70
<211> LENGTH: 50
<212> TYPE: DNA
<213> ORGANISM: Escherichia coli

<400> SEQUENCE: 70
tgtgcatttt tgtgtacggg gctgtcaccc tgtatcgcac gcctttccag    50

<210> SEQ ID NO 71
<211> LENGTH: 50
<212> TYPE: DNA
<213> ORGANISM: Escherichia coli

<400> SEQUENCE: 71
ccagccacaa gtcatccgct aatttttcaa cattagtcgg ttcggtcctc    50

<210> SEQ ID NO 72
<211> LENGTH: 50
<212> TYPE: DNA
<213> ORGANISM: Klebsiella pneumoniae

<400> SEQUENCE: 72
cttcgactgg tctcagctcc atccgcaggg acttcaccta cacaccagcg                50

<210> SEQ ID NO 73
<211> LENGTH: 50
<212> TYPE: DNA
<213> ORGANISM: Klebsiella pneumoniae

<400> SEQUENCE: 73
tttgagttcc cggccgaacc gctggcaaca aaggataagg gttgcgctcg                50

<210> SEQ ID NO 74
<211> LENGTH: 50
<212> TYPE: DNA
<213> ORGANISM: Klebsiella pneumoniae

<400> SEQUENCE: 74
gggatttcac atccgacttg acagaccgcc tgcgtgcgct ttacgcccag                50

<210> SEQ ID NO 75
<211> LENGTH: 50
<212> TYPE: DNA
<213> ORGANISM: Klebsiella pneumoniae

<400> SEQUENCE: 75
aacccttggt cttccggcga gcgggctttt cacccgcttt atcgttactt                50

<210> SEQ ID NO 76
<211> LENGTH: 50
<212> TYPE: DNA
<213> ORGANISM: Klebsiella pneumoniae

<400> SEQUENCE: 76
acagcctgtg cattttggtg tacgggacta tcaccctgta ccgtcggact                50

<210> SEQ ID NO 77
<211> LENGTH: 50
<212> TYPE: DNA
<213> ORGANISM: Klebsiella pneumoniae

<400> SEQUENCE: 77
cacggttcat tagtaccggt tagctcaacg catcgctgcg cttacacacc                50

<210> SEQ ID NO 78
<211> LENGTH: 50
<212> TYPE: DNA
<213> ORGANISM: Klebsiella pneumoniae

<400> SEQUENCE: 78
gctgtaacgg ttcatatcac cttaccgacg cttttcgcag attagcacgt                50

<210> SEQ ID NO 79
<211> LENGTH: 50
<212> TYPE: DNA
<213> ORGANISM: Pseudomonas aeruginosa

<400> SEQUENCE: 79

<210> SEQ ID NO 80
<211> LENGTH: 50
<212> TYPE: DNA
<213> ORGANISM: Proteus mirabilis

<400> SEQUENCE: 80
gagttcacaa taacagcatc ttcagatacg gggctatcac cctttactgc          50

<210> SEQ ID NO 81
<211> LENGTH: 50
<212> TYPE: DNA
<213> ORGANISM: Pseudomonas aeruginosa

<400> SEQUENCE: 81
cgatcggttt tatgggatta gctccacctc gcggcttggc aacccttttgt         50

<210> SEQ ID NO 82
<211> LENGTH: 50
<212> TYPE: DNA
<213> ORGANISM: Pseudomonas aeruginosa

<400> SEQUENCE: 82
gtcgccttgg taggccttta ccccaccaac tagctaatcc gacctaggct          50

<210> SEQ ID NO 83
<211> LENGTH: 50
<212> TYPE: DNA
<213> ORGANISM: Pseudomonas aeruginosa

<400> SEQUENCE: 83
agatttcagc ctaccacctt aaacttggac aaccaacgcc aagctggcct          50

<210> SEQ ID NO 84
<211> LENGTH: 50
<212> TYPE: DNA
<213> ORGANISM: Pseudomonas aeruginosa

<400> SEQUENCE: 84
ccggcaatgc cactggcgtg acaaccggaa caccagaggt tcgtccactc          50

<210> SEQ ID NO 85
<211> LENGTH: 50
<212> TYPE: DNA
<213> ORGANISM: Pseudomonas aeruginosa

<400> SEQUENCE: 85
gctttcgcta cgcctaccct atacggttaa gcttgccact gaatataagt          50

<210> SEQ ID NO 86
<211> LENGTH: 50
<212> TYPE: DNA
<213> ORGANISM: Pseudomonas aeruginosa

<400> SEQUENCE: 86
gaggaaatga agcgcagcgg agagatcgag gagatactgc agcgctaccg          50

<210> SEQ ID NO 87
<211> LENGTH: 50
<212> TYPE: DNA
<213> ORGANISM: Pseudomonas aeruginosa

<400> SEQUENCE: 87

-continued

```
ggtgagctgc atggtgcggg actccgcaga ggttccggtg aagcgatac          50

<210> SEQ ID NO 88
<211> LENGTH: 50
<212> TYPE: DNA
<213> ORGANISM: Staphylococcus sp.

<400> SEQUENCE: 88
ccctcagttc atccgctcac ttttcaacgt aagtcggttc ggtcctccat          50

<210> SEQ ID NO 89
<211> LENGTH: 50
<212> TYPE: DNA
<213> ORGANISM: Staphylococcus sp.

<400> SEQUENCE: 89
accagcgcct ccacgtaagc tagcgctcac gtttcaaagg ctcctaccta          50

<210> SEQ ID NO 90
<211> LENGTH: 50
<212> TYPE: DNA
<213> ORGANISM: Streptococcus agalactiae

<400> SEQUENCE: 90
agttaccgtc acttggtaga ttttccactc ctaccaacgt tcttctctaa          50

<210> SEQ ID NO 91
<211> LENGTH: 50
<212> TYPE: DNA
<213> ORGANISM: Streptococcus agalactiae

<400> SEQUENCE: 91
tgtctccgat agggattgcc tatctgggtt agagtagcca taacacaagg          50

<210> SEQ ID NO 92
<211> LENGTH: 50
<212> TYPE: DNA
<213> ORGANISM: Streptococcus agalactiae

<400> SEQUENCE: 92
cagctcagcc ttaatgagta ccggatttgc ctaatactca gccttactgc          50

<210> SEQ ID NO 93
<211> LENGTH: 50
<212> TYPE: DNA
<213> ORGANISM: Stenotrophomonas maltophilia

<400> SEQUENCE: 93
ccgtcgccgg cttgcagccc tctgtcccta ccattgtagt acgtgtgtag          50

<210> SEQ ID NO 94
<211> LENGTH: 50
<212> TYPE: DNA
<213> ORGANISM: Stenotrophomonas maltophilia

<400> SEQUENCE: 94
atggtcaagc cgcacggatc attagtatca gttagctcaa tacattgctg          50

<210> SEQ ID NO 95
<211> LENGTH: 50
<212> TYPE: DNA
<213> ORGANISM: Staphylococcus aureus
```

-continued

<400> SEQUENCE: 95
agtgacagca agaccgtctt tcactttcga accatgcggt tcaaaatatt    50

<210> SEQ ID NO 96
<211> LENGTH: 50
<212> TYPE: DNA
<213> ORGANISM: Staphylococcus aureus

<400> SEQUENCE: 96
cttcacccca atcatttgtc ccaccttcga cggctagttc ctaaaaggtt    50

<210> SEQ ID NO 97
<211> LENGTH: 50
<212> TYPE: DNA
<213> ORGANISM: Staphylococcus aureus

<400> SEQUENCE: 97
tccctaataa cagagtttta cgatccgaag accttcatca ctcacgcggc    50

<210> SEQ ID NO 98
<211> LENGTH: 50
<212> TYPE: DNA
<213> ORGANISM: Staphylococcus aureus

<400> SEQUENCE: 98
aattccactt tcctcttctg cactcaagtt ttccagtttc caatgaccct    50

<210> SEQ ID NO 99
<211> LENGTH: 50
<212> TYPE: DNA
<213> ORGANISM: Staphylococcus aureus

<400> SEQUENCE: 99
aaagcttact tacagctccc caaagcatat cgtcgttagt aacgtccttc    50

<210> SEQ ID NO 100
<211> LENGTH: 50
<212> TYPE: DNA
<213> ORGANISM: Staphylococcus aureus

<400> SEQUENCE: 100
aagccaacat cctagttgtc tgggcaacgc cacatccttt tccacttaac    50

<210> SEQ ID NO 101
<211> LENGTH: 50
<212> TYPE: DNA
<213> ORGANISM: Staphylococcus aureus

<400> SEQUENCE: 101
ttataggtgg tacaggaata tcaacctgtt atccatcgcc tacgcctgtc    50

<210> SEQ ID NO 102
<211> LENGTH: 50
<212> TYPE: DNA
<213> ORGANISM: Staphylococcus aureus

<400> SEQUENCE: 102
tttgggctct tcccgtttcg ctcgccgcta ctaagggaat cgaattttct    50

<210> SEQ ID NO 103
<211> LENGTH: 50
<212> TYPE: DNA
<213> ORGANISM: Staphylococcus aureus

<210> SEQ ID NO 103

<400> SEQUENCE: 103
tcttcacagg tactatgatt tcaccgagtc tctcgttgag acagtgccca            50

<210> SEQ ID NO 104
<211> LENGTH: 50
<212> TYPE: DNA
<213> ORGANISM: Staphylococcus aureus

<400> SEQUENCE: 104
ctcgcgtacc gctttaatgg gcgaacagcc caacccttgg gaccgactac            50

<210> SEQ ID NO 105
<211> LENGTH: 50
<212> TYPE: DNA
<213> ORGANISM: Staphylococcus aureus

<400> SEQUENCE: 105
gaacttcaac ctgaccaagg gtagatcacc tggtttcggg tctacgacca            50

<210> SEQ ID NO 106
<211> LENGTH: 50
<212> TYPE: DNA
<213> ORGANISM: Staphylococcus aureus

<400> SEQUENCE: 106
gcctggcaac gttctactct agcggaacgt aagttcgact accatcgacg            50

<210> SEQ ID NO 107
<211> LENGTH: 100
<212> TYPE: DNA
<213> ORGANISM: Acinetobacter baumannii

<400> SEQUENCE: 107
catcatggcc cttacggcca gggctacaca cgtgctacaa tggtcggtac aaagggttgc    60
tacacagcga tgtgatgcta atctcaaaaa gccgatcgta                         100

<210> SEQ ID NO 108
<211> LENGTH: 100
<212> TYPE: DNA
<213> ORGANISM: Acinetobacter baumannii

<400> SEQUENCE: 108
ctttatgtcc tctaaagagc cgttcgagac taggacgttg ataggttgga tgtggaagca    60
tagtgatatg tgaagctgac caatactaat tgctcgtgag                         100

<210> SEQ ID NO 109
<211> LENGTH: 100
<212> TYPE: DNA
<213> ORGANISM: Candida albicans

<400> SEQUENCE: 109
ttgttgcagt taaaaagctc gtagttgaac cttgggcttg gctggccggt ccatcttttt    60
gatgcgtact ggacccagcc gagcctttcc ttctgggtag                         100

<210> SEQ ID NO 110
<211> LENGTH: 100
<212> TYPE: DNA
<213> ORGANISM: Candida albicans

<400> SEQUENCE: 110

```
taacagctta tcaccctgga attggtttat ccggagatgg ggtcttaggg ctggaagagc    60
gcggtaattt tgccgcgtcc ggtgcgctta cgacggtcct                         100

<210> SEQ ID NO 111
<211> LENGTH: 100
<212> TYPE: DNA
<213> ORGANISM: Enterobacter cloacae

<400> SEQUENCE: 111
ccagagtctg aatcagcttg tgtgttagtg gaagcgtctg gaaagtcgca cggtacaggg    60
tgaaagtccc gtacacgaaa acacacaggc tgtgaactcg                         100

<210> SEQ ID NO 112
<211> LENGTH: 100
<212> TYPE: DNA
<213> ORGANISM: Escherichia coli

<400> SEQUENCE: 112
cggtggagca tgtggtttaa ttcgatgcaa cgcgaagaac cttacctggt cttgacatcc    60
acagaacctt gtagagatac gagggtgcct tcgggaactg                         100

<210> SEQ ID NO 113
<211> LENGTH: 100
<212> TYPE: DNA
<213> ORGANISM: Escherichia coli

<400> SEQUENCE: 113
gcacgaatgg cgtaatgatg gccaggctgt ctccacccga gactcagtga aattgaactc    60
gctgtgaaaa gaatgcaagt gtaacccgcg gcaagacgga                         100

<210> SEQ ID NO 114
<211> LENGTH: 100
<212> TYPE: DNA
<213> ORGANISM: Enterococcus faecalis

<400> SEQUENCE: 114
gcatgcgatt ggaagtgcat gtccaagcaa tgagtcttga gtagagttaa atgctttact    60
ctctaaggac aagttgtgac ggggagcgaa ataatagtag                         100

<210> SEQ ID NO 115
<211> LENGTH: 100
<212> TYPE: DNA
<213> ORGANISM: Enterococcus faecium

<400> SEQUENCE: 115
aacacgtggg taacctgccc atcagaaggg gataacactt ggaaacaggt gctaataccg    60
tataacaatc gaaaccgcat ggttttgatt tgaaaggcgc                         100

<210> SEQ ID NO 116
<211> LENGTH: 100
<212> TYPE: DNA
<213> ORGANISM: Enterococcus faecium

<400> SEQUENCE: 116
tgtaggactc caatatggta gttctttcag atagtcgaat gacttggaaa agtcagtcaa    60
agagggtaaa accccgtag acgaaatgtg gaagacacct                          100

<210> SEQ ID NO 117
<211> LENGTH: 100
```

```
<212> TYPE: DNA
<213> ORGANISM: Escherichia coli

<400> SEQUENCE: 117
gtgaatacgt tcccgggcct tgtacacacc gcccgtcaca ccatgggagt gggttgcaaa      60
agaagtaggt agcttaacct tcggagggc gcttaccact                           100

<210> SEQ ID NO 118
<211> LENGTH: 100
<212> TYPE: DNA
<213> ORGANISM: Escherichia coli

<400> SEQUENCE: 118
ggagggggat aactactgga aacggtagct aataccgcat aacgtcgcaa gaccaaagag      60
ggggaccctc gggcctcttg ccatcggatg tgcccagatg                           100

<210> SEQ ID NO 119
<211> LENGTH: 100
<212> TYPE: DNA
<213> ORGANISM: Escherichia coli

<400> SEQUENCE: 119
gaagagtttg atcatggctc agattgaacg ctggcggcag gcctaacaca tgcaagtcga      60
acggtaacag gaagcagctt gctgtttcgc tgacgagtgg                           100

<210> SEQ ID NO 120
<211> LENGTH: 100
<212> TYPE: DNA
<213> ORGANISM: Escherichia coli

<400> SEQUENCE: 120
caagcggtgg agcatgtggt ttaattcgat gcaacgcgaa gaaccttacc tggtcttgac      60
atccacggaa gttttcagag atgagaatgt gccttcggga                           100

<210> SEQ ID NO 121
<211> LENGTH: 100
<212> TYPE: DNA
<213> ORGANISM: Escherichia coli

<400> SEQUENCE: 121
tggcttagaa gcagccatca tttaaagaaa gcgtaatagc tcactggtcg agtcggcctg      60
cgcggaagat gtaacggggc taaaccatgc accgaagctg                           100

<210> SEQ ID NO 122
<211> LENGTH: 100
<212> TYPE: DNA
<213> ORGANISM: Escherichia coli

<400> SEQUENCE: 122
aaagagtaac ggaggagcac gaaggttggc taatcctggt cggacatcag gaggttagtg      60
caatggcata agccagcttg actgcgagcg tgacggcgcg                           100

<210> SEQ ID NO 123
<211> LENGTH: 100
<212> TYPE: DNA
<213> ORGANISM: Escherichia coli

<400> SEQUENCE: 123
aacggggagc agcccagagc ctgaatcagt gtgtgtgtta gtggaagcgt ctggaaaggc      60
```

```
gtgcgataca gggtgacagc cccgtacaca aaaatgcaca                           100
```

<210> SEQ ID NO 124
<211> LENGTH: 100
<212> TYPE: DNA
<213> ORGANISM: Escherichia coli

<400> SEQUENCE: 124

```
aacccggtga tctagccatg ggcaggttga aggttgggta acactaactg gaggaccgaa    60
ccgactaatg ttgaaaaatt agcggatgac ttgtggctgg                          100
```

<210> SEQ ID NO 125
<211> LENGTH: 100
<212> TYPE: DNA
<213> ORGANISM: Klebsiella pneumoniae

<400> SEQUENCE: 125

```
ctcgggtgaa ggaactaggc aaaatggtgc cgtaacttcg ggagaaggca cgctggtgtg    60
taggtgaagt ccctgcggat ggagctgaga ccagtcgaag                          100
```

<210> SEQ ID NO 126
<211> LENGTH: 100
<212> TYPE: DNA
<213> ORGANISM: Klebsiella pneumoniae

<400> SEQUENCE: 126

```
gcatggctgt cgtcagctcg tgttgtgaaa tgttgggtta agtcccgcaa cgagcgcaac    60
ccttatcctt tgttgccagc ggttcggccg ggaactcaaa                          100
```

<210> SEQ ID NO 127
<211> LENGTH: 100
<212> TYPE: DNA
<213> ORGANISM: Klebsiella pneumoniae

<400> SEQUENCE: 127

```
cgtgccagca gccgcggtaa tacggagggt gcaagcgtta atcggaatta ctgggcgtaa    60
agcgcacgca ggcggtctgt caagtcggat gtgaaatccc                          100
```

<210> SEQ ID NO 128
<211> LENGTH: 100
<212> TYPE: DNA
<213> ORGANISM: Klebsiella pneumoniae

<400> SEQUENCE: 128

```
aggtgtgctg tgaggcatgc tggaggtatc agaagtgcga atgctgacat aagtaacgat    60
aaagcgggtg aaaagcccgc tcgccggaag accaagggtt                          100
```

<210> SEQ ID NO 129
<211> LENGTH: 100
<212> TYPE: DNA
<213> ORGANISM: Klebsiella pneumoniae

<400> SEQUENCE: 129

```
gagcagccca gagtctgaat cagcttgtgt gttagtggaa cggtctggaa agtccgacgg    60
tacagggtga tagtcccgta caccaaaatg cacaggctgt                          100
```

<210> SEQ ID NO 130
<211> LENGTH: 100
<212> TYPE: DNA
<213> ORGANISM: Klebsiella pneumoniae

<400> SEQUENCE: 130
gactttaagt ctcctgaagg aacgttgaag acgacgacgt tgataggccg ggtgtgtaag    60
cgcagcgatg cgttgagcta accggtacta atgaaccgtg                         100

<210> SEQ ID NO 131
<211> LENGTH: 100
<212> TYPE: DNA
<213> ORGANISM: Klebsiella pneumoniae

<400> SEQUENCE: 131
agcgactaag cgtacacggt ggatgccctg gcagtcagag gcgatgaagg acgtgctaat    60
ctgcgaaaag cgtcggtaag gtgatatgaa ccgttacagc                         100

<210> SEQ ID NO 132
<211> LENGTH: 100
<212> TYPE: DNA
<213> ORGANISM: Pseudomonas aeruginosa

<400> SEQUENCE: 132
aggccgagag ctgatgacga gtcgtctttt agatgacgaa gtggttgatg ccatgcttcc    60
aagaaaagct tctaagcttc aggtaaccag gaaccgtacc                         100

<210> SEQ ID NO 133
<211> LENGTH: 100
<212> TYPE: DNA
<213> ORGANISM: Proteus mirabilis

<400> SEQUENCE: 133
cccagagtct taatcaatag cagtgtcagg agaacggtct ggaaagtccg gcagtaaagg    60
gtgatagccc cgtatctgaa gatgctgtta ttgtgaactc                         100

<210> SEQ ID NO 134
<211> LENGTH: 100
<212> TYPE: DNA
<213> ORGANISM: Pseudomonas aeruginosa

<400> SEQUENCE: 134
gtcatcatgg cccttacggc cagggctaca cacgtgctac aatggtcggt acaaagggtt    60
gccaagccgc gaggtggagc taatcccata aaaccgatcg                         100

<210> SEQ ID NO 135
<211> LENGTH: 100
<212> TYPE: DNA
<213> ORGANISM: Pseudomonas aeruginosa

<400> SEQUENCE: 135
acgtcctgag ggagaaagtg ggggatcttc ggacctcacg ctatcagatg agcctaggtc    60
ggattagcta gttggtgggg taaaggccta ccaaggcgac                         100

<210> SEQ ID NO 136
<211> LENGTH: 100
<212> TYPE: DNA
<213> ORGANISM: Pseudomonas aeruginosa

<400> SEQUENCE: 136
gttaatattc ctgtacttct ggttactgcg atggagggac ggagaaggct aggccagctt    60
ggcgttggtt gtccaagttt aaggtggtag gctgaaatct                         100

<210> SEQ ID NO 137
<211> LENGTH: 100
<212> TYPE: DNA
<213> ORGANISM: Pseudomonas aeruginosa

<400> SEQUENCE: 137
ccgtggacgt ttgagatttg agagggctg ctcctagtac gagaggaccg gagtggacga    60
acctctggtg ttccggttgt cacgccagtg gcattgccgg                        100

<210> SEQ ID NO 138
<211> LENGTH: 100
<212> TYPE: DNA
<213> ORGANISM: Pseudomonas aeruginosa

<400> SEQUENCE: 138
gggagcctac ttgttaggtg actgcgtacc ttttgtataa tgggtcagcg acttatattc    60
agtggcaagc ttaaccgtat agggtaggcg tagcgaaagc                        100

<210> SEQ ID NO 139
<211> LENGTH: 100
<212> TYPE: DNA
<213> ORGANISM: Pseudomonas aeruginosa

<400> SEQUENCE: 139
ccgcctccat ttcaggcccg ccattttccg cacgccgccg ccgttcttat cggtagcgct    60
gcagtatctc ctcgatctct ccgctgcgct tcatttcctc                        100

<210> SEQ ID NO 140
<211> LENGTH: 100
<212> TYPE: DNA
<213> ORGANISM: Pseudomonas aeruginosa

<400> SEQUENCE: 140
cagtatctcc tcgatctctc cgctgcgctt catttcctcg aacgtcttca gtatcgcttc    60
caccggaacc tctgcggagt cccgcaccat gcagctcacc                        100

<210> SEQ ID NO 141
<211> LENGTH: 100
<212> TYPE: DNA
<213> ORGANISM: Staphylococcus sp.

<400> SEQUENCE: 141
cgaaaccagg tgatctaccc ttggtcaggt tgaagttcag gtaacactga atggaggacc    60
gaaccgactt acgttgaaaa gtgagcggat gaactgaggg                        100

<210> SEQ ID NO 142
<211> LENGTH: 100
<212> TYPE: DNA
<213> ORGANISM: Staphylococcus sp.

<400> SEQUENCE: 142
tggagcttta ctgtagcctg atattgaaat tcggcacagc ttgtacagga taggtaggag    60
cctttgaaac gtgagcgcta gcttacgtgg aggcgctggt                        100

<210> SEQ ID NO 143
<211> LENGTH: 100
<212> TYPE: DNA
<213> ORGANISM: Streptococcus agalactiae

<400> SEQUENCE: 143

```
gagcaacgcc gcgtgagtga agaaggtttt cggatcgtaa agctctgttg ttagagaaga    60
acgttggtag gagtggaaaa tctaccaagt gacggtaact                         100

<210> SEQ ID NO 144
<211> LENGTH: 100
<212> TYPE: DNA
<213> ORGANISM: Streptococcus agalactiae

<400> SEQUENCE: 144
cctatgataa cgggacgcca gtttcgtttg aggcgttgtt gggatactac ccttgtgtta    60
tggctactct aacccagata ggcaatccct atcggagaca                         100

<210> SEQ ID NO 145
<211> LENGTH: 100
<212> TYPE: DNA
<213> ORGANISM: Streptococcus agalactiae

<400> SEQUENCE: 145 gggggacgc agtaggatag gcgaagcgtg cgattggatt gcacgtctaa gcagtaaggc     60
tgagtattag gcaaatccgg tactcattaa ggctgagctg                         100

<210> SEQ ID NO 146
<211> LENGTH: 100
<212> TYPE: DNA
<213> ORGANISM: Stenotrophomonas maltophilia

<400> SEQUENCE: 146
cggaggaagg tggggatgac gtcaagtcat catggccctt acggccaggg ctacacacgt    60
actacaatgg tagggacaga gggctgcaag ccggcgacgg                         100

<210> SEQ ID NO 147
<211> LENGTH: 100
<212> TYPE: DNA
<213> ORGANISM: Stenotrophomonas maltophilia

<400> SEQUENCE: 147
cctgaaggaa ccatgtagac tacgtggttg ataggtcagg tgtgtaagta cagcaatgta    60
ttgagctaac tgatactaat gatccgtgcg gcttgaccat                         100

<210> SEQ ID NO 148
<211> LENGTH: 100
<212> TYPE: DNA
<213> ORGANISM: Staphylococcus aureus

<400> SEQUENCE: 148
cctacctata agactgggat aacttcggga aaccggagct aataccggat aatattttga    60
accgcatggt tcgaaagtga aagacggtct tgctgtcact                         100

<210> SEQ ID NO 149
<211> LENGTH: 100
<212> TYPE: DNA
<213> ORGANISM: Staphylococcus aureus

<400> SEQUENCE: 149
acaccgcccg tcacaccacg agagtttgta acacccgaag ccggtggagt aacctttag     60 gaactagccg tcgaaggtgg gacaaatgat tggggtgaag                         100

<210> SEQ ID NO 150
```

```
<211> LENGTH: 100
<212> TYPE: DNA
<213> ORGANISM: Staphylococcus aureus

<400> SEQUENCE: 150
aggcagcagt agggaatctt ccgcaatggg cgaaagcctg acggagcaac gccgcgtgag      60
tgatgaaggt cttcggatcg taaaactctg ttattaggga                           100

<210> SEQ ID NO 151
<211> LENGTH: 100
<212> TYPE: DNA
<213> ORGANISM: Staphylococcus aureus

<400> SEQUENCE: 151
gcgtaggcgg ttttttaagt ctgatgtgaa agcccacggc tcaaccgtgg agggtcattg      60
gaaactggaa aacttgagtg cagaagagga aagtggaatt                           100

<210> SEQ ID NO 152
<211> LENGTH: 100
<212> TYPE: DNA
<213> ORGANISM: Staphylococcus aureus

<400> SEQUENCE: 152
gattaagtta ttaagggcgc acggtggatg ccttggcact agaagccgat gaaggacgtt      60
actaacgacg atatgctttg gggagctgta agtaagcttt                           100

<210> SEQ ID NO 153
<211> LENGTH: 100
<212> TYPE: DNA
<213> ORGANISM: Staphylococcus aureus

<400> SEQUENCE: 153
tgttcgaaag ggaaacagcc cagaccacca gctaaggtcc caaatatat gttaagtgga      60 aaaggatgtg gcgttgccca gacaactagg atgttggctt                           100

<210> SEQ ID NO 154
<211> LENGTH: 100
<212> TYPE: DNA
<213> ORGANISM: Staphylococcus aureus

<400> SEQUENCE: 154
ccagaggaag gctcgtccgc tctgggttag tcgggtccta agctgaggcc gacaggcgta      60
ggcgatggat aacaggttga tattcctgta ccacctataa                           100

<210> SEQ ID NO 155
<211> LENGTH: 100
<212> TYPE: DNA
<213> ORGANISM: Staphylococcus aureus

<400> SEQUENCE: 155
agaaggcaca cccggagaac tgaaacatct tagtacccgg aggaagagaa agaaaattcg      60
attcccttag tagcggcgag cgaaacggga agagcccaaa                           100

<210> SEQ ID NO 156
<211> LENGTH: 100
<212> TYPE: DNA
<213> ORGANISM: Staphylococcus aureus

<400> SEQUENCE: 156
cgaaattcct tgtcgggtaa gttccgaccc gcacgaaagg cgtaacgatt tgggcactgt      60
```

```
ctcaacgaga gactcggtga aatcatagta cctgtgaaga                       100

<210> SEQ ID NO 157
<211> LENGTH: 100
<212> TYPE: DNA
<213> ORGANISM: Staphylococcus aureus

<400> SEQUENCE: 157
tcgacgggga ggtttggcac ctcgatgtcg gctcatcgca tcctggggct gtagtcggtc   60
ccaagggttg ggctgttcgc ccattaaagc ggtacgcgag                       100

<210> SEQ ID NO 158
<211> LENGTH: 100
<212> TYPE: DNA
<213> ORGANISM: Staphylococcus aureus

<400> SEQUENCE: 158
gtaaatgtgg agccgtagcg aaagcgagtc tgaatagggc gtttagtatt tggtcgtaga   60
cccgaaacca ggtgatctac ccttggtcag gttgaagttc                       100

<210> SEQ ID NO 159
<211> LENGTH: 100
<212> TYPE: DNA
<213> ORGANISM: Staphylococcus aureus

<400> SEQUENCE: 159
aaggaggtca cacctgttcc catgccgaac acagaagtta agctccttag cgtcgatggt   60 agtcgaacttc acgttccgct agagtagaac gttgccaggc                      100
```